United States Patent [19]

Karjalainen et al.

[11] Patent Number: 5,439,928

[45] Date of Patent: Aug. 8, 1995

[54] AROMATASE INHIBITING 4(5)-IMIDAZOLES

[75] Inventors: Arto J. Karjalainen; Reino O. Pelkonen; Marja-Liisa Sodervall, all of Oulu; Matti A. Lahde; Risto A. S. Lammintausta, both of Turku; Arja L. Karjalainen; Arja M. Kalapudas, both of Oulu, all of Finland

[73] Assignee: Orion-yhtyma Oy, Espoo, Finland

[21] Appl. No.: 63,471

[22] Filed: May 19, 1993

Related U.S. Application Data

[63] Continuation-in-part of Ser. No. 16,547, Feb. 11, 1993, abandoned, which is a continuation-in-part of Ser. No. 870,779, Apr. 21, 1992, abandoned, and Ser. No. 993,827, Dec. 18, 1992, abandoned, which is a continuation of Ser. No. 501,699, Mar. 30, 1990, abandoned, said Ser. No. 870,779, is a continuation of Ser. No. 761,550, Sep. 18, 1991, abandoned.

[51] Int. Cl.⁶ .................. A61K 31/415; C07D 233/64
[52] U.S. Cl. ..................... 514/400; 514/396; 548/335.1; 548/336.1; 548/340.1; 548/341.1
[58] Field of Search ............. 548/335.1, 336.1, 340.1, 548/341.1; 514/396, 400

[56] References Cited

U.S. PATENT DOCUMENTS

| | | | |
|---|---|---|---|
| 4,544,664 | 10/1985 | Karjalainen et al. | 514/396 |
| 5,006,543 | 4/1991 | Boyle | 548/262.2 |
| 5,098,923 | 5/1992 | Karjalainen et al. | 514/396 |

*Primary Examiner*—Patricia L. Morris
*Attorney, Agent, or Firm*—Ronald J. Kubovcik

[57] ABSTRACT

Novel 4(5)-imidazole derivatives of specified formula and their non-toxic salts possess selective aromatase inhibiting properties, which are valuable in the treatment of estrogen dependent diseases e.g. breast cancer.

27 Claims, No Drawings

AROMATASE INHIBITING 4(5)-IMIDAZOLES

This application is a continuation-in-part of application Ser. No. 08/016,547 filed Feb. 11, 1993, which is, in turn, a continuation-in-part of application Ser. No. 07/870,779 filed Apr. 21, 1992, now abandoned, and application Ser. No. 07/993,827 filed Dec. 18, 1992, now abandoned. Application Ser. No. 07/870,779 is a continuation of application Ser. No. 07/761,550 filed Sep. 18, 1991, now abandoned, and application Ser. No. 07/993,827 is a continuation of application Ser. No. 07/501,699 filed Mar. 30, 1990, and now abandoned.

The present invention relates to substituted imidazole derivatives and their non-toxic, pharmaceutically acceptable acid addition salts, and their preparation, to pharmaceutical compositions containing the same and their use.

The imidazole derivatives of the present invention have the general formulae (Ia) and (Ic):

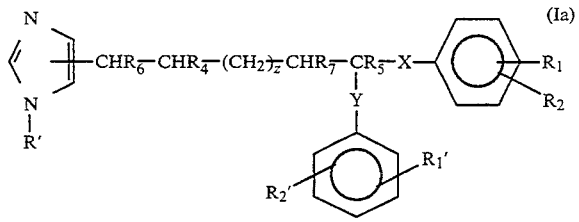
(Ia)

wherein $R_1$, $R_2$, $R'_1$ and $R'_2$, which can be the same or different, are H, $CH_3$, $C_2H_5$, $C_3H_7$, $OCH_3$, OH, $CH_2OH$, $NO_2$, $NH_2$, CN, $CF_3$, $CHF_2$, $CH_2F$ or halogen; R' is H or

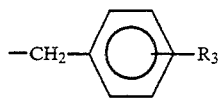

where $R_3$ is H, $CH_3$ or halogen; $R_4$ is H, $R_5$ is H or OH, $R_6$ is H or OH and $R_7$ is H or $R_4$ and $R_6$ together form a bond or $R_5$ and $R_7$ together form a bond; X and Y, which can be the same or different, are a bond, a straight $C_{1-2}$-alkyl or the corresponding alkenyl and z is 0 to 2 and

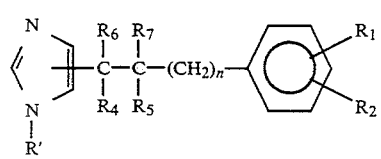
(Ic)

wherein one of $R_6$ and $R_7$ is H and the other is

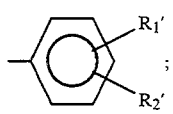
;

$R_1$, $R_2$, $R'_1$ and $R'_2$ which can be the same or different are H, $CH_3$, $C_2H_5$, $C_3H_7$, $OCH_3$, OH, $CH_2OH$, $NO_2$, $NH_2$, CN, $CF_3$, $CHF_2$, $CH_2F$ or halogen; R' is H or

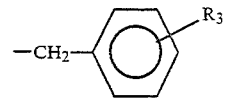

where $R_3$ is H, $CH_3$ or halogen; $R_4$ is H or OH; $R_5$ is H or OH or $R_4$ and $R_5$ together form a bond and n is 1 to 4, except that when $R_5$ is OH, $R_6$ must be H.

Compounds of formula (Ic) include compounds of formula (Ib)

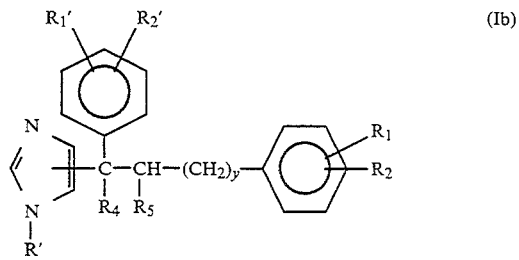
(Ib)

wherein $R_1$, $R_2$, $R'_1$ and $R'_2$, which can be the same or different, are H, $CH_3$, $C_2H_5$, $C_3H_7$, $OCH_3$, OH, $CH_2OH$, $NO_2$, $NH_2$, CN, $CF_3$, $CHF_2$, $CH_2F$ or halogen; R' is H or

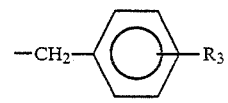

where $R_3$ is H, $CH_3$ or halogen; $R_4$ is H or OH and $R_5$ is H or $R_4$ and $R_5$ together form a bond and y is 0 to 4; and compounds of formula (Id)

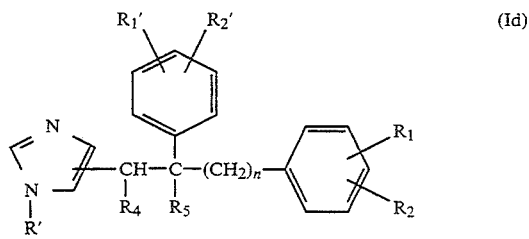
(Id)

wherein $R_1$, $R_2$, $R'_1$ and $R'_2$, which can be the same or different, are H, $CH_3$, $C_2H_5$, $C_3H_7$, $OCH_3$, $NO_2$, $NH_2$, CN, $CF_3$, $CHF_2$, $CH_2F$ or halogen; R' is H or

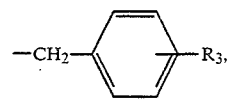, where $R_3$ is H, $CH_3$ or halogen; $R_4$ is H or OH and $R_5$ is H or OH or $R_4$ and $R_5$ together form a bond and n 1 to 4.

The non-toxic pharmaceutically acceptable acid addition salts of these compounds are also within the scope of the invention.

The compounds of formulae (Ia) and (Ic) form acid addition salts with both organic and inorganic acids. They can thus form many pharmaceutically usable acid addition salts, as, for instance, chlorides, bromides, sulfates, nitrates, phosphates, sulfonates, formates, tartrates, maleates, citrates, benzoates, salicylates, ascorbates and the like.

The invention includes within its scope pharmaceutical compositions comprising at least one of the compounds of formula (Ia) or (Ic) or a non-toxic, pharmaceutically acceptable salt thereof, and a compatible pharmaceutically acceptable carrier therefor.

The compounds of the present invention have been found, depending on the substituents R', $R_1$, $R_2$, $R'_1$ and $R'_2$, to possess varying degrees of aromatase and desmolase inhibiting properties. Among them there are very selective enzyme aromatase inhibiting compounds which are valuable in the treatment of estrogen dependent diseases, e.g. breast cancer, or benign prostatic hyperplasia (BPH).

In formula (Ia) preferred compounds include those in which $R_4$, $R_5$, $R_6$ and $R_7$ are H; compounds in which $R_1$, $R_2$, $R'_1$ and $R'_2$ are each H; compounds in which one of the phenyl rings is mono-substituted, preferably in the para position and preferably with a methoxy group, and the other is unsubstituted; compounds in which each phenyl ring is monosubstituted, preferably in the para positions and preferably with a halogen such as fluorine; compounds in which one phenyl ring is unsubstituted and the other is disubstituted in the 3 and 4 or 3 and 5 positions; compounds in which $R_4$ and $R_5$ form a bond and compounds in which R' is H.

In formula (Ic) preferred compounds include those in which $R_4$ and $R_5$ are both H; compounds in which R' is H, compounds in which both phenyl groups are unsubstituted; compounds in which both phenyl groups are mono-substituted, preferably in the para position with F, CN or $CH_3$; compounds in which one phenyl group is unsubstituted and the other is monosubstituted in the para position, preferably with F; compounds in which one phenyl group is monosubstituted in the para position and the other is disubstituted in the 3 and 5 or 2 and 6 positions.

Compounds of formula (Ia) can be prepared by the following methods. Compounds of formula (Ia) wherein the branches

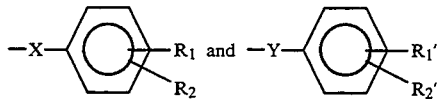

are identical, can be prepared by a successive sequence of reactions comprising a Grignard reaction of 4(5)-imidazole derivative of the formula (IIa)

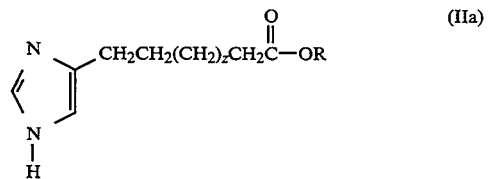

or its 1-benzyl derivative (IIIa) with an appropriate aryl-or arylalkylmagnesium halide (IVa) following the loss of water and hydrogenation.

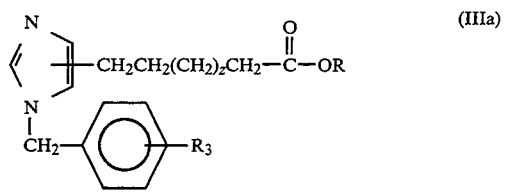

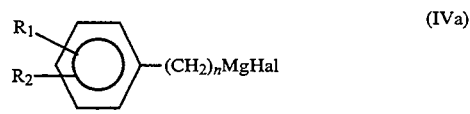

In the formulae (IIa) to (IVa) R is alkyl, preferably lower alkyl, n is 0 to 2 and Hal is halogen. The first reaction step, the Grignard reaction, leads to the following compounds of formula (Ia):

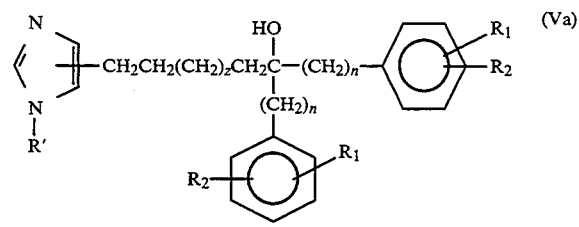

In this reaction the aryl- or arylalkylmagnesium halide derivative can be, for example, an aryl- or arylalkylmagnesiumbromide derivative, which is prepared by reacting the corresponding aryl- or arylalkylbromide derivative with magnesium. The Grignard reagent (IVa) cannot be prepared if $R_1$ and/or $R_2$ are OH, $CH_2OH$ or $NH_2$. Suitable solvents for the reaction include a variety of ethers, preferably tetrahydrofuran.

The aryl- or arylalkylmagnesiumhalide derivative is prepared in the usual way by adding the aryl- or arylalkylhalide derivative in a suitable solvent, e.g. tetrahydrofuran, dropwise onto magnesium turnings covered by tetrahydrofuran, at the boiling point of the reaction mixture. When the magnesium turnings have reacted, the mixture is cooled slightly and the 4(5)-imidazole derivative (IIa) or its 1-benzylsubstituted derivative (IIIa) is added in solid form in small portions or dropwise in tetrahydrofuran. After the addition, the reaction mixture is refluxed until all of the 4(5)-imidazole derivative has reacted. The reaction time varies between one and five hours.

According to the feature of the invention, the compounds of formula (Ia), wherein $R_7$ and $R_5$ both are hydrogen or together form a bond, are prepared by dehydration of the compounds of formula (Ia), where $R_5$ is OH, and by catalytic addition of hydrogen in the second step. Water is eliminated by usual methods, i.e. by heating with concentrated hydrochloric acid or by heating with dry potassium hydrogen sulfate. The unsaturated compounds (VIa) (the compounds of formula (Ia) wherein $R_7$ and $R_5$ together form a bond) are isolated and after that hydrogenated. Alternatively they can be hydrogenated directly in an acidic medium without previous isolation. The hydrogenation is conveniently carried out at room temperature with good stirring in alcohol, e.g. ethanol in the presence of a catalyst in a hydrogen atmosphere. Suitable catalysts are for example platinium oxide, palladium-on-carbon or Raney-nickel.

The reaction scheme for these steps can be illustrated as follows:

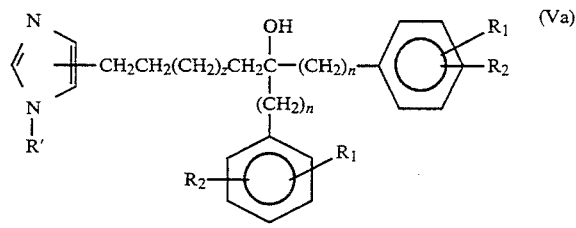

wherein R', R$_1$, R$_2$, z and n are as defined before

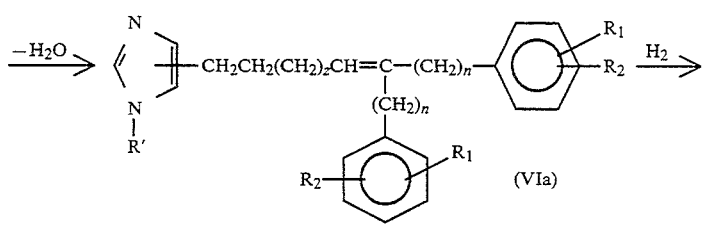

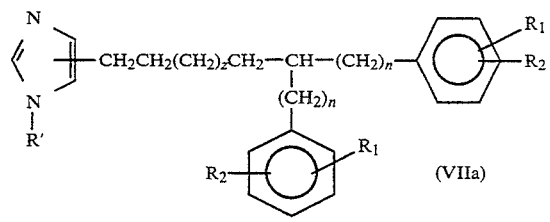

If R' is a substituted or unsubstituted benzyl, this group may be removed by hydrogenation as well. In this case the hydrogenation is performed in an acidic medium such as hydrochloric acid-ethanol mixture at elevated temperature.

The reaction scheme of this hydrogenation which leads to compounds of formula (Ia) wherein R', R$_7$ and R$_5$ each are hydrogen can be illustrated as follows:

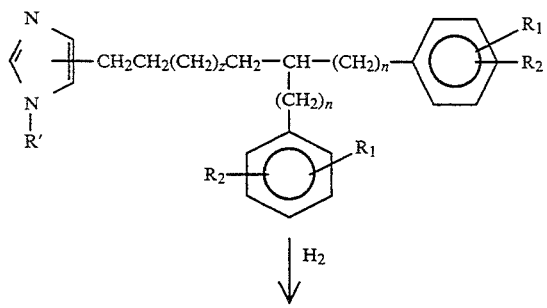

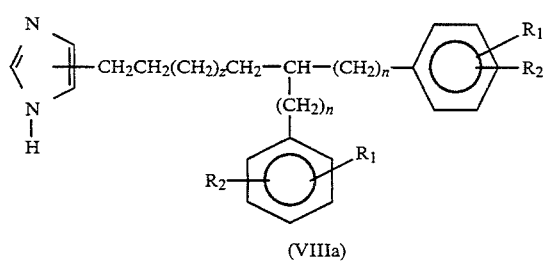

wherein R$_1$, R$_2$, z and n are as defined before.

Another method to remove the benzylic R' group is a hydrogen transfer reaction in which the starting compound (VIIa) is refluxed with ammonium formate and 10% Pd/C in an appropriate lower alcohol, such as methanol or ethanol, or its aqueous solution. The compounds (VIIIa) can also be prepared directly from the compounds (VIa) by hydrogen transfer reaction with ammonium formate or by hydrogenating both the double bond and the protecting benzyl group at the same time. The compounds (VIIIa) can also be prepared directly from the compounds (Va) by hydrogen transfer reaction in which the starting compound (Va) is refluxed with ammonium formate and 10% Pd/C in an acidic medium such as acetic acid.

The compounds of formula (VIIIa) can also be prepared from the compounds of formula (Va) wherein R' is a substituted or unsubstituted benzyl by removing first the benzylic R' by a hydrogen transfer reaction as described before to give the compounds of formula (IXa)

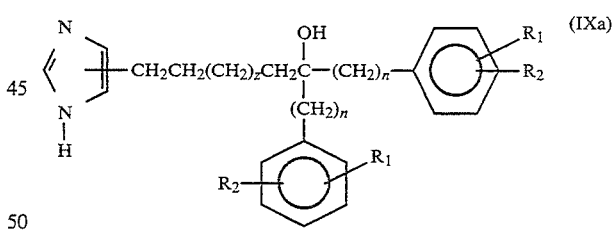

wherein R$_1$, R$_2$, z and n are as defined before.

The benzylic R' can be removed by hydrogenation as well. The compounds of formula (IXa) are further dehydrated by the methods described before to form the compounds of formula (Ia) where R$_5$ and R$_7$ together form a bond (Xa).

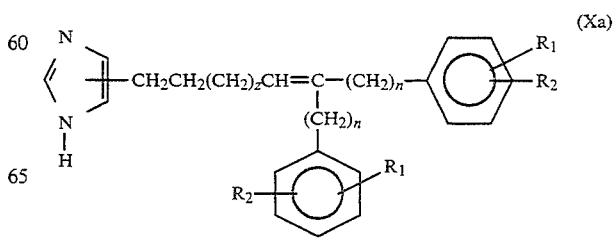

The compounds of formula (Xa) are further hydrogenated by the methods described before to give the compounds of formula (VIIIa).

When the compounds of formula (Ia) wherein $R_1$ and/or $R_2$ are OH, $CH_2OH$ or $NH_2$ are wanted, they can be prepared by the following reactions.

The compounds of formula (Ia) wherein $R_1$ and/or $R_2$ are OH can be prepared by reacting the 4(5)-imidazole derivative (IIa) or (IIIa) with a Grignard reagent (IVa) where $R_1$ and/or $R_2$ are $OCH_2Ph$ or OTHP (THP=tetrahydropyranyl) and then hydrogenating catalytically by the methods described to hydrogenate the benzylic R' group. If R' is a protecting benzyl group it will be removed conveniently at the same time. Another method is to dealkylate the compounds of formula (Ia) where $R_1$ and/or $R_2$ are $OCH_3$ by allowing them to react with $BBr_3$, for example.

The compounds of formula (Ia) wherein $R_1$ and/or $R_2$ are $CH_2OH$ may be prepared from the corresponding compounds where $R_1$ and/or $R_2$ are CN by conventional methods, i.e. by hydrolyzing the nitrile group and then catalytical reduction of the acid group.

The compounds of formula (Ia) wherein $R_1$ and/or $R_2$ are $NH_2$ can be prepared by hydrogenating the corresponding compounds where $R_1$ and/or $R_2$ are $NO_2$. The protecting benzyl group will be hydrogenated as well.

The compounds of formula (Ia) wherein $R_1$ and/or $R_2$ are CN can be prepared from the corresponding compounds where $R_1$ and/or $R_2$ are $NH_2$ by diazotization. Compounds of formula (Ia) wherein $R_1$ and/or $R_2$ are halogen may also optionally be prepared by the same method.

Compounds of formula (Ia) where R' is a benzyl group can be prepared by benzylating the corresponding compounds where R' is hydrogen. The starting compound is first treated with a strong base such as sodium hydroxide in water or sodium hydride in an appropriate solvent, e.g. dimethyl formamide, to give the alkali metal salt of the imidazole and then in the second step adding to this benzyl halide. The reaction scheme can be illustrated as follows:

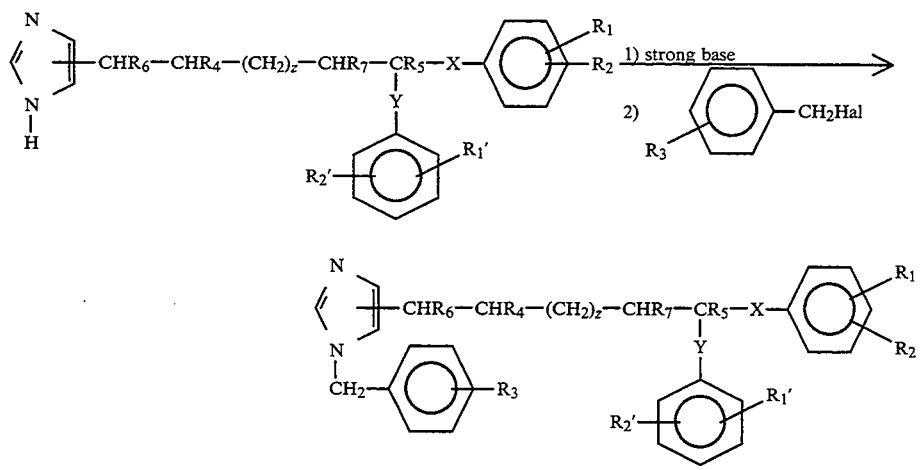

The free OH, $CH_2OH$ and $NH_2$ substituents must be protected during the benzylation reaction.

Another process for the preparations of compounds of formula (Ia) wherein the branches

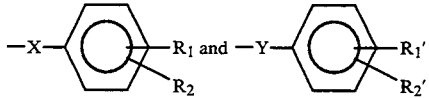

are different, comprises in the first stage a series of two successive Grignard reactions starting from 4(5)-imidazole derivative (IIa) or its 1-benzyl substituted derivative (IIIa) as previously. Now, however, the amount of the Grignard reagent is reduced as well as the reaction temperature, to stop the reaction at the ketone stage to give the ketone (XIa), which further is reacted with another Grignard reagent (XIIa) to give a compound of formula (Ia) where $R_5$ is OH. The reactions are illustrated as follows:

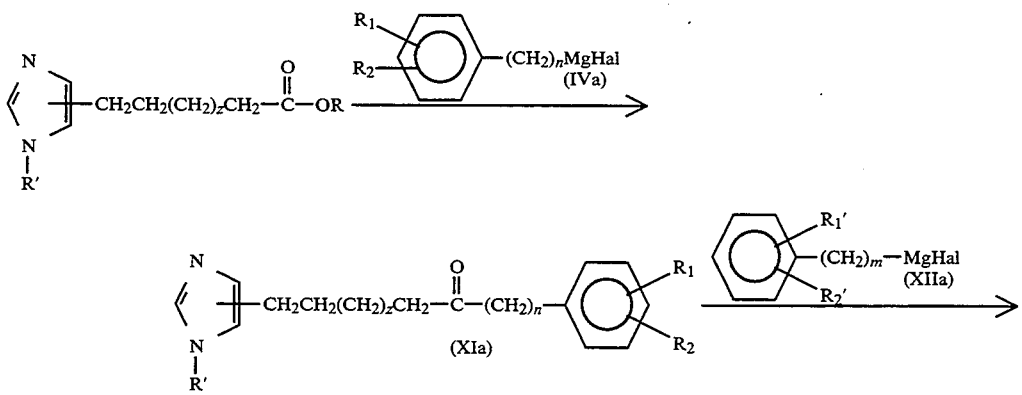

-continued

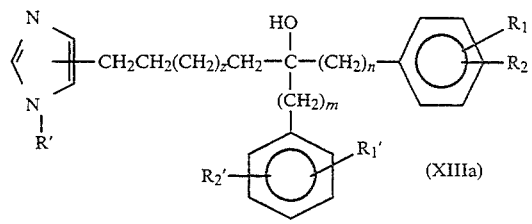
(XIIIa)

In the reaction scheme above m and n, which can be the same or different, are 0 to 2, z is 0 to 2 and R is an alkyl group, preferably a lower alkyl. The compounds of formula (XIIIa) are further dehydrated and hydrogenated by the methods described before to give the compounds of formula

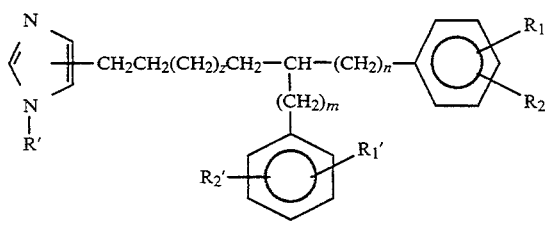

wherein R′, $R_1$, $R_2$, $R'_1$, $R'_2$, z, n and m are as defined before.

The Grignard reagents (IVa) and (XIIa) cannot be prepared when the substituents are OH, $CH_2OH$ or $NH_2$. When the compounds of formula (Ia), wherein one or more of the substituents $R_1$, $R_2$, $R'_1$ and $R'_2$ are OH are wanted they can be prepared by the following method.

The compounds of formula (Ia) wherein one or more of the substituents $R_1$, $R_2$, $R'_1$ and $R'_2$ are OH can be prepared by reacting the 4(5)-imidazole derivative (IIa) or (IIIa) first with a Grignard reagent (IVa) and then with reagent (XIIa) where the substituent/substituents of either compound (IVa) or (XIIa) or both of them are $OCH_2Ph$ or OTHP and hydrogenating catalytically by the methods described to hydrogenate the benzylic R′ group. The protecting benzyl group will be removed conveniently at the same time. Another method is to dealkylate the compounds of formula (Ia) where the substituent/substituents are $OCH_3$ by allowing them to react with $BBr_3$, for example.

The compounds of formula (Ia) wherein one or more of the substituents $R_1$, $R_2$, $R'_1$ and $R'_2$ are $CH_2OH$, $NH_2$ or CN can be prepared by the methods described before.

In order to achieve a better control of the reactions above, the starting material may be an amide

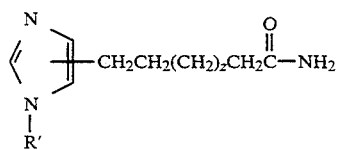

or a nitrile

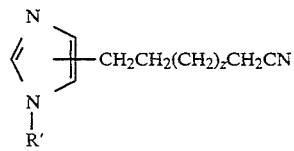

as well.

Choosing appropriate conditions for the dehydration of the compounds of formula (Ia) where $R_5$ is OH results in the corresponding compounds of formula (Ia) where one of the alkyl chains X or Y is transformed to the corresponding alkenyl chain.

The starting compounds of the formulae (IIa) and (IIIa) may be prepared for example from 4(5)-imidazole alkyl acid of the formula

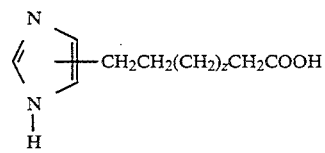

and its 1-benzyl derivative of the formula

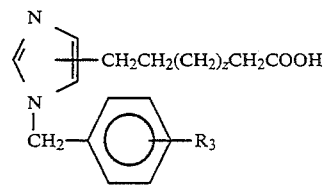

wherein z and $R_3$ are as defined before, by esterifying them according to the method described in U.S. Pat. No. 3,759,944.

A further method of preparing the compounds of formula (Ia) is the Wittig reaction where the starting compound is an 4(5)-imidazole aldehyde (XIVa). In the formula (XIVa) R′ is as defined before.

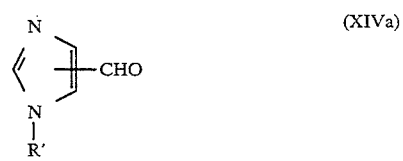
(XIVa)

In the Wittig reaction the first step is to prepare a phosphonium salt (XVa) from the corresponding halogenated hydrocarbon (XVIa) by reacting it with triphenylphosphine. The reaction scheme can be illustrated as follows:

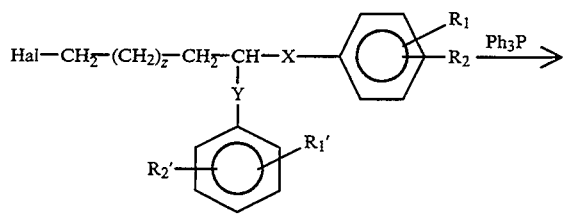

phosphorus ylide which is further allowed to react with the 4(5)-imidazole aldehyde (XIVa) to achieve the compounds of formula (Ia) wherein $R_4$ and $R_6$ together form a bond (XVIIa). The strong base can be NaH or BuLi in a proper solvent such as dimethoxyethane, tetrahydrofuran or DMF. Further alkali metal alkoxides the corresponding alcohols as solvent and NaH in DMSO can be used as proton acceptors. The compounds (XVIIa) are isolated and after that hydrogenated as has been described before to achieve the compounds of formula (Ia) wherein $R_4$ and $R_6$ both are hydrogen. The reaction scheme for these steps can be illustrated as follows:

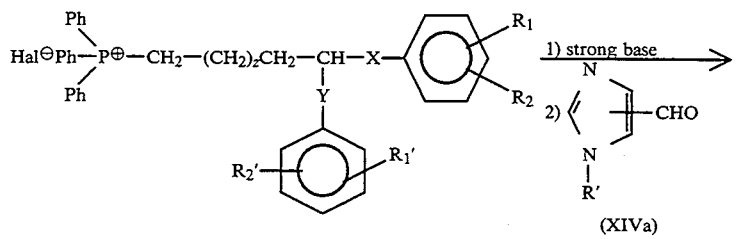

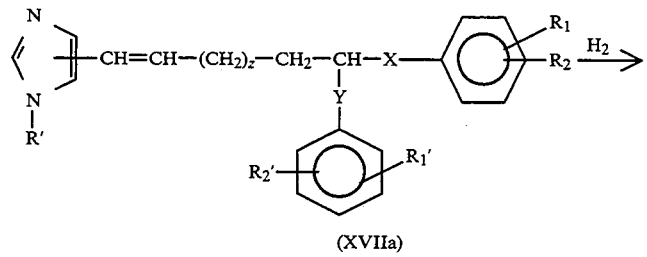

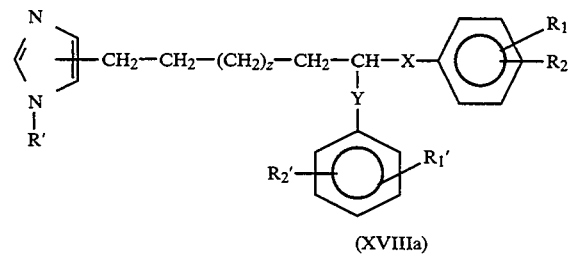

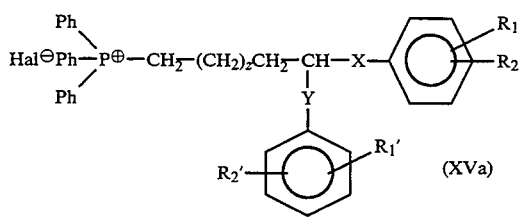

in which $R_1$, $R_2$, $R'_1$, $R'_2$, X, Y and z are as defined before and Hal is halogen.

In the second step of the Wittig-reaction the compound (XVa) is treated with a strong base to form a The Wittig reaction can be performed in another order i.e. a phosphonium salt (XIXa) is prepared from the corresponding halogenated 4(5)-imidazole derivative (XXa) by reacting it with triphenylphosphine. In the second step the compound (XIXa) is allowed to react with a strong base and then with a substituted ketone of the formula (XXIa) as described before to give the compounds of formula (Ia) wherein $R_5$ and $R_7$ together form a bond (XXIIa). The reaction scheme for these steps can be illustrated as follows:

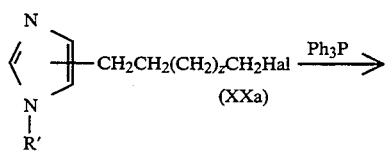

-continued

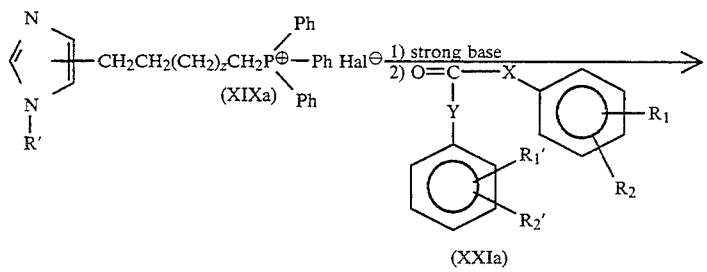

(XXIa)

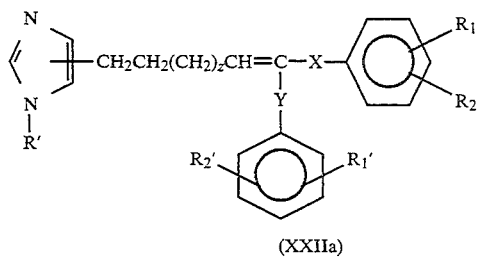

(XXIIa)

wherein R', $R_1$, $R_2$, $R'_1$, $R'_2$, z, X and Y are as defined before.

The compounds of formula (Ia) can also be prepared by a modified Wittig reaction, namely the Horner-Emmons or Wadsworth-Emmons reaction where the phosphonate (XXIIIa) which is prepared from the halogenated hydrocarbon (XVIa) and a triester of phosphonic acid (e.g. (EtO)$_3$P) by the Arbuzow reaction reacts firstly with a base (e.g. NaH in DMSO or in dimethoxyethane) and then with the aldehyde (XIVa). The product (XVIIa) formed is a compound of formula (Ia) where $R_4$ and $R_6$ together form a bond. The reaction scheme can be illustrated as follows:

In the formula (XXIIIa) R is alkyl with 1–4 carbon atoms and $R_1$, $R_2$, $R'_1$, $R'_2$, X, Y and z are as defined before. The unsaturated compounds (XVIIa) are further hydrogenated to form the compounds of formula (Ia) wherein $R_4$ and $R_6$ both are hydrogen. The benzylic R' group and the double bond of the compounds of formula (XVIIa) can be removed at the same time by the methods described before.

Another useful method to prepare compounds of formula (Ia) is the Grignard reaction in which the 4(5)-imidazole aldehyde (XIVa) is allowed to react with a Grignard reagent (XXIVa) to give a compound of formula (Ia) where $R_6$ is OH (XXVa). The Grignard rea-

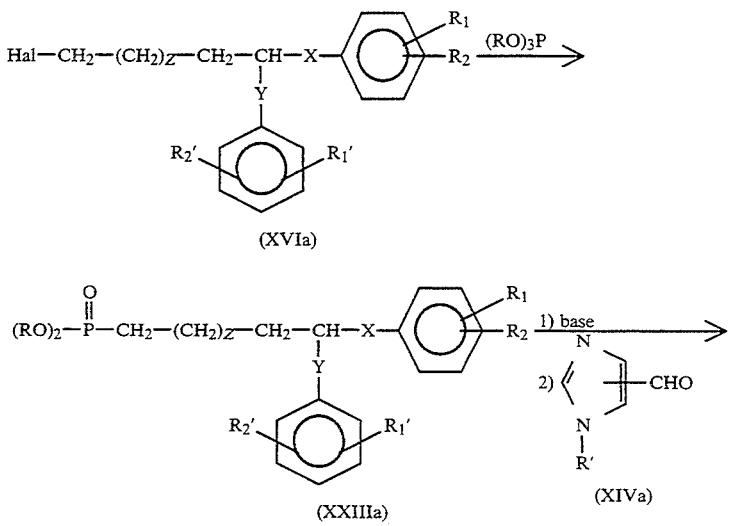

(XVIa)

(XXIIIa)       (XIVa)

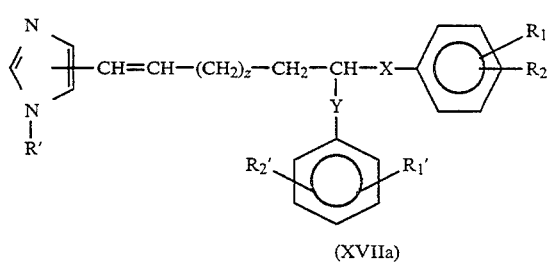

(XVIIa)

gent is prepared by reacting the corresponding halogenated hydrocarbon with magnesium turnings in the usual way. The compound (XXVa) is further dehydrated by heating with KHSO₄ to achieve the compounds of formula (Ia) where R₄ and R₆ together form a bond (XVIIa).

The unsaturated derivatives are then hydrogenated to form the compounds of formula (Ia) wherein R₄ and R₆ both are hydrogen. The reaction scheme for these steps can be illustrated as follows:

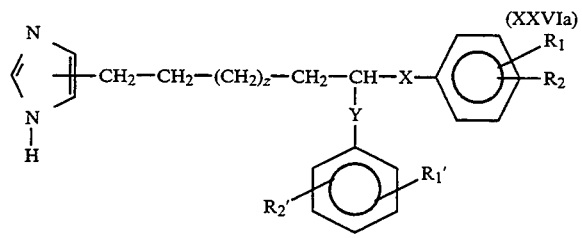

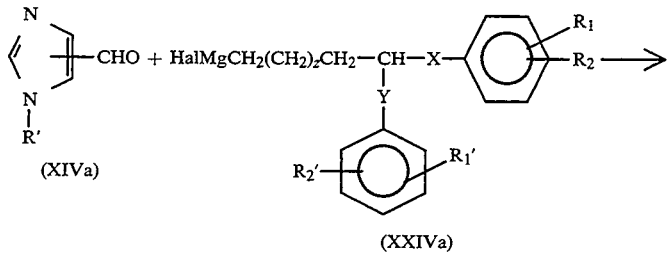

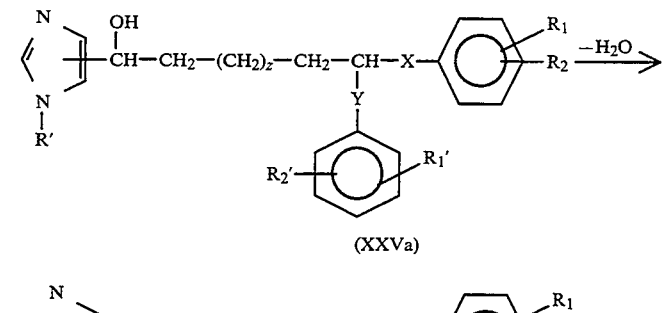

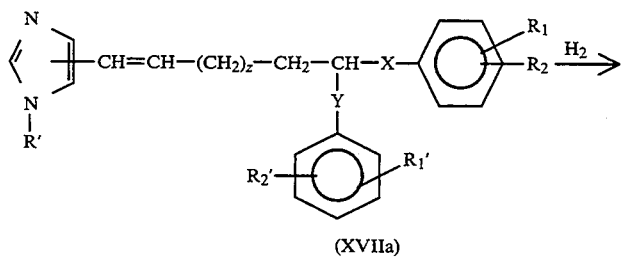

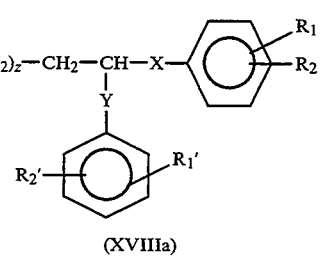

In the formulae (XXVa), (XVIIa) and (XVIIIa) R', R₁, R₂, R'₁, R'₂, X, Y and z are as defined before.

If R' is substituted or unsubstituted benzyl, this group may be removed by hydrogenation and hydrogen transfer reaction as described before to give the compounds of formula (XXVIa).

The compounds of formula (XXVIa) can also be prepared directly from the compounds (XVIIa) and (XXVa) by the methods described before.

The Grignard reagent (XXIVa) cannot be prepared when the substituents are OH, CH₂OH or NH₂. The compounds of formula (Ia) wherein one or more of the substituents R₄, R₂, R'₁ and R'₂ are OH, CH₂OH or NH₂ can be prepared according to the methods described before.

Further method to prepare the compounds of formula (Ia) wherein one or more of the substituents R₁, R₂, R'₁ and R'₂ are NO₂ is nitration of the corresponding compounds wherein one or more of the substituents R₁, R₂, R'₁ and R'₂ are H.

Compounds of the formula (Ic) can be prepared by preparing a compound of formula (Ib) or (Id).

Compounds of formula (Ib) can be prepared by the following methods.

Compounds of formula (Ib) can be prepared by a successive sequence of reactions comprising firstly a Grignard reaction of 4(5)-imidazole aldehyde (IIb)

$$\underset{\underset{R'}{|}}{\overset{N}{\underset{N}{\bigg\langle}}}\!\!\!\!\!=\!\!\!\!-CHO \qquad (IIb)$$

with an appropriate arylalkylmagnesiumhalide (IIIb) tive in a suitable solvent, e.g. tetrahydrofuran, dropwise onto magnesium turnings covered by tetrahydrofuran, at the boiling point of the reaction mixture. When the magnesium turnings have reacted, the mixture is cooled slightly and the 4(5)-imidazole aldehyde (IIb) is added in solid form in small portions or dropwise in tetrahydrofuran. After the addition, the reaction mixture is refluxed until all of the 4(5)-imidazole aldehyde (IIb) has reacted. The reaction time varies between one and five hours.

The compounds (IVb) are further oxidized for example with manganese dioxide to achieve compounds of formula (Vb) which are allowed to react with another Grignard reagent (VIb) to give the compounds of formula (Ib) where $R_4$ is OH (VIIb). The reaction scheme for these steps can be illustrated as follows:

[Structure (IVb) → oxidation]

[Structure (Vb) + (VIb) → (VIIb)]

[Structure HalMgCH₂(CH₂)ᵧ-aryl with R₁, R₂]

which leads to following compounds (IVb)

[Structure (IVb)]

In the reaction the arylalkylmagnesium halide derivative can be, for example, an arylalkylmagnesiumbromide derivative, which is prepared by reacting the corresponding arylalkylbromide derivative with magnesium. Suitable solvents for the reaction include a variety of ethers, preferably tetrahydrofuran.

The arylalkyimagnesiumhalide derivative is prepared in the usual way by adding the arylalkylhalide deriva- The arylmagnesium halide (VIb) is prepared by reacting the corresponding halogenated aromatic compound with magnesium turnings in the usual way.

Compounds of formula (Ib) can also be prepared by reacting an 4(5)-imidazole aldehyde (IIb) with an arylmagnesiumhalide (VIb) which leads to following compounds (VIIIb)

[Structure (VIIIb)]

The compounds (VIIIb) are further oxidized for example with manganese dioxide to achieve the compounds of formula (IXb) which are further allowed to react with the Grignard reagent (IIIb) to give the compounds of formula (Ib) where $R_4$ is OH (VIIb). The reaction scheme for these steps can be illustrated as follows:

[Structure (VIIIb) → oxidation → (IXb) + (IIIb) →]

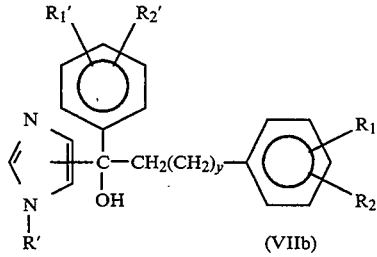

According to the feature of the invention, the compounds of formula (Ib), wherein $R_4$ and $R_5$ both are hydrogen or together form a bond, are prepared by dehydration of the compounds of formula (Ib), where $R_4$ is OH, and by catalytic addition of hydrogen in the second step. Water is eliminated by usual methods, i.e. by heating with concentrated hydrochloric acid or by heating with dry potassium hydrogen sulfate. The unsaturated compounds (Xb) (the compounds of formula (Ib) wherein $R_4$ and $R_5$ together form a bond) are isolated and after that hydrogenated. Alternatively they can be hydrogenated directly in an acidic medium without previous isolation. The hydrogenation is conveniently carried out at room temperature with good stirring in alcohol, e.g. ethanol in the presence of a catalyst in a hydrogen atmosphere. Suitable catalysts are for example platinium oxide, palladium-on-carbon or Raney-nickel.

The reaction scheme for these steps can be illustrated as follows:

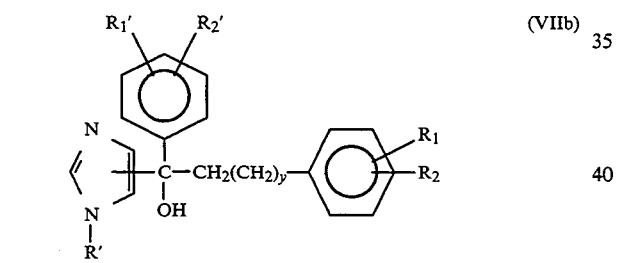

wherein R', $R_1$, $R_2$, $R'_1$, $R'_2$ and y are as defined before

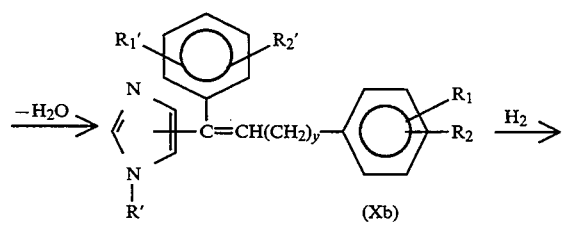

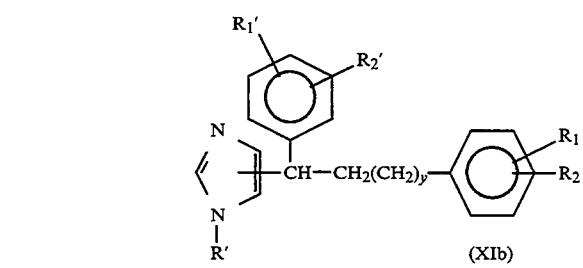

wherein R', $R_1$, $R_2$, $R'_1$, $R'_2$ and y are as defined before.

If R' is a substituted or unsubstituted benzyl, this group may be removed by hydrogenation as well. In this case the hydrogenation is performed in an acidic medium such as hydrochloricacid-ethanol mixture at elevated temperature.

The reaction scheme of this hydrogenation which leads to compounds of formula (Ib) wherein R', $R_4$ and $R_5$ each are hydrogen can be illustrated as follows:

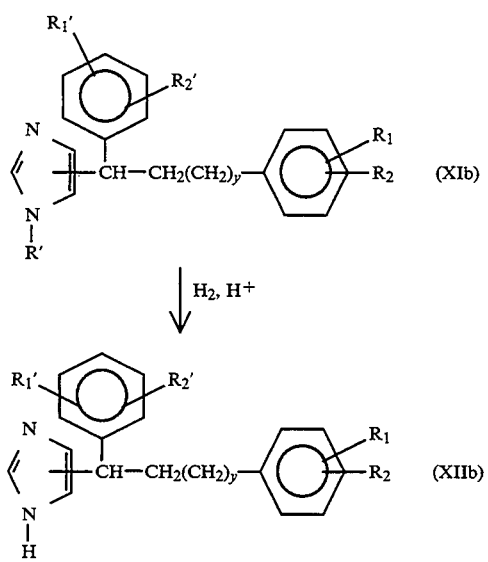

Another method to remove the benzylic R' group is a hydrogen transfer reaction in which the starting compound (XIb) is refluxed with ammonium formate and 10% Pd/C in an appropriate alcohol, such as methanol or ethanol, or its aqueous solution. The compounds (XIIb) can also be prepared directly from the compounds (Xb) by hydrogen transfer reaction with ammonium formate or by hydrogenating both the double bond and the protecting benzyl group at the same time. The compounds (XIIb) can also be prepared directly from the compounds (VIIb) by hydrogen transfer reaction in which the starting compound (VIIb) is refluxed with ammonium formate and 10% Pd/C in an acidic medium such as acetic acid.

The compounds of formula (XIIb) can also be prepared from the compounds of formula (VIIb) wherein R' is a substituted or unsubstituted benzyl by removing first the benzylic R' by a hydrogen transfer reaction by the method described before to give the compounds of formula (XIIIb)

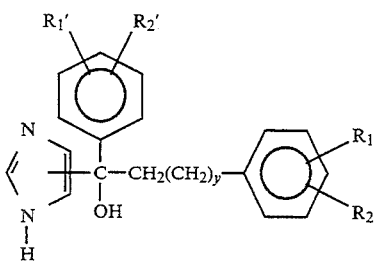

(XIIIb)

wherein $R_1$, $R_2$, $R'_1$, $R'_2$ and y are as defined before. The benzylic R' can be removed by hydrogenation as well. The compounds of formula (XIIIb) are further dehydrated by the methods described before to form the compounds of formula (Ib) where $R_4$ and $R_5$ together form a bond (XIVb).

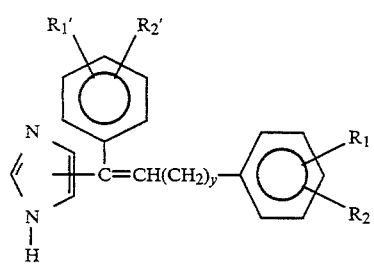

(XIVb)

The compounds of formula (XIVb) are further hydrogenated by the methods described before to give the compounds of formula (XIIb).

The benzylic R' can be removed already before the oxidizing reaction by the methods described before. The reaction scheme for this hydrogenation can be illustrated as follows:

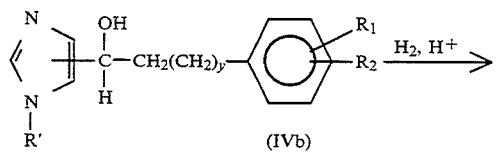

(IVb)

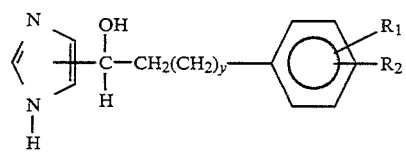

The Grignard reagents (IIIb) and (VIb) cannot be prepared when the substituents are OH, $CH_2OH$ or $NH_2$. The compounds of formula (Ib) wherein one or more of the substituents $R_1$, $R_2$, $R'_1$ and $R'_2$ are OH, $CH_2OH$ or $NH_2$ can be prepared by the following methods.

The compounds of formula (Ib) wherein one or more of the substituents $R_1$, $R_2$, $R'_1$ and $R'_2$ are OH can be prepared by reacting the 4(5)-imidazole derivative (IIb) first with a Grignard reagent (IIIb) and then with reagent (VIb) or revise order where the substituent/substituents of either compound (IIIb) or (VIb) or both of them are $OCH_2Ph$ or OTHP (THP=tetrahydropyranyl) and then hydrogenating catalytically by the methods described to hydrogenate the benzylic R' group. If R' is a protecting benzyl group it will be removed conveniently at the same time. Another method is to dealkylate the compounds of formula (Ib) where the substituent/substituents are $OCH_3$ by allowing them to react with $BBr_3$, for example.

The compounds of formula (Ib) wherein one or more of the substituents $R_1$, $R_2$, $R'_1$ and $R'_2$ are $CH_2OH$ may be prepared from the corresponding compounds where the substituent/substituents are CN by conventional methods, i.e. by hydrolyzing the nitrile group and then reducing the acid group.

The compounds of formula (Ib) wherein one or more of the substituents $R_1$, $R_2$, $R'_1$ and $R'_2$ are $NH_2$ can be prepared by hydrogenating the corresponding compounds where the substituent/substituents are $NO_2$. The protecting benzyl group will be hydrogenated as well.

The compounds of formula (Ib) wherein one or more of the substituents $R_1$, $R_2$, $R'_1$ and $R'_2$ are CN can be prepared from the corresponding compounds where one or more of the substituents are $NH_2$ by diazotization. Compounds of formula (Ib) wherein one or more of the substituents $R_1$, $R_2$, $R'_1$ and $R'_2$ are halogen may also optionally be prepared by the same method.

Another method of preparing compounds of formula (Ib) is a McMurry reaction which comprises a reductive coupling of a benzoylimidazole (IXb)

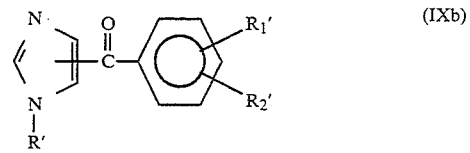

(IXb)

and an appropriate aldehyde of the formula (XVb)

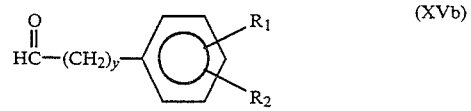

(XVb)

in an appropriate solvent, such as tetrahydrofuran or dimethoxyethane, in the presence of a low valent titanium reagent in an inert atmosphere, e.g. in nitrogen or argon, to give the compounds of formula (Ib) where $R_4$ and $R_5$ together form a bond (Xb)

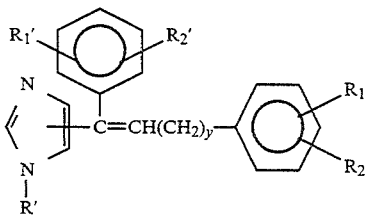

(Xb)

The unsaturated compounds (Xb) are further hydrogenated as described before. The aldehyde (XVb) is prepared from the corresponding alcohol in the usual way.

When the compounds of formula (Xb) where $R'_1$ and/or $R'_2$ are $CH_2OH$, $NH_2$ or CN are wanted they can be prepared by the methods described before.

The compounds of formula (Xb) where $R'_1$ and/or $R'_2$ are OH and $R_1$ and $R_2$ are as defined before can be prepared by a McMurry reaction from the compounds of formula (IXb) where $R'_1$ and/or $R'_2$ are OH which can be prepared by hydrogenating catalytically the compounds of formula (IXb) wherein R′$_1$ and/or R′$_2$ are OCH$_2$Ph or OTHP by the methods described before. Alternatively the hydrogenation can be done before the oxidizing reaction. If R′ is a protecting benzyl group it will be removed conveniently at the same time. Another method is to dealkylate the compounds of formula (IXb) where R′$_1$ and/or R′$_2$ are OCH$_3$ by allowing them to react with BBr$_3$, for example.

Compounds of formula (Ib) wherein R′$_1$ and/or R′$_2$ are OH and R$_1$ and R$_2$ are as defined before can be prepared by a McMurry reaction in which the aldehyde (XVb) is allowed to react with a ketone (IXb) wherein R′$_1$ and/or R′$_2$ are OCH$_2$Ph or OTHP to give a compound of formula (Xb) where R′$_1$ and/or R′$_2$ are OCH$_2$Ph or OTHP and R$_1$ and R$_2$ are as defined before which is further hydrogenated to give compounds of formula (XIIb) where R′$_1$ and/or R′$_2$ are OH.

Compounds of formula (Ib) where R′ is a benzyl can be prepared by benzylating the corresponding compounds where R′ is hydrogen. The starting compound is first treated with a strong base such as sodium hydroxide in water or sodium hydride in an appropriate solvent, e.g. dimethyl formamide, to give the alkali metal salt of the imidazole and then in the second step adding to this benzyl halide. The reaction scheme can be illustrated as follows:

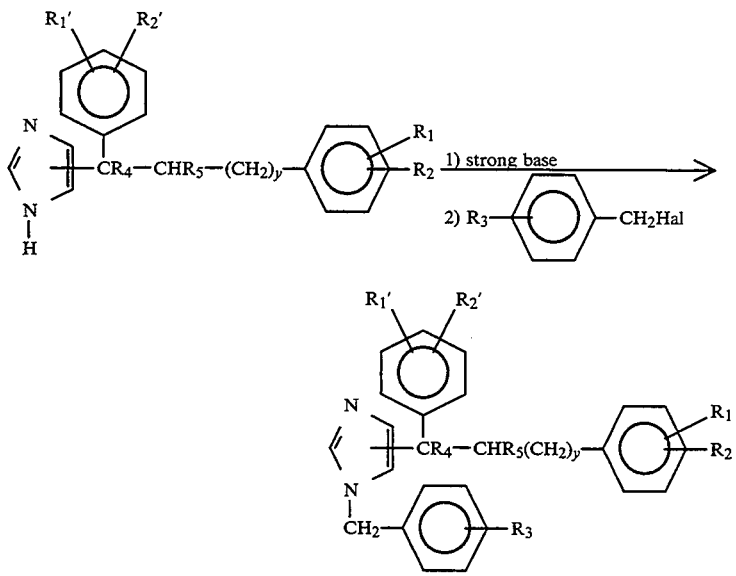

The free OH, CH$_2$OH and NH$_2$ substituents must be protected during the benzylation reaction.

Further method to prepare the compounds of formula (Ib) wherein one or more of the substituents R$_1$, R$_2$, R′$_1$ and R′$_2$ are NO$_2$ is nitration of the corresponding compounds where one or more of the substituents are H.

Compounds of formula (Id) can be prepared by McMurry reaction which comprises a reductive coupling of a diphenylketone (IId)

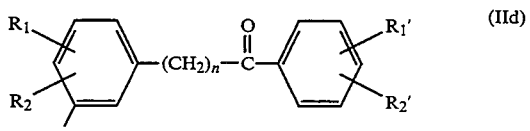

wherein R$_1$, R$_2$, R′$_1$ and R′$_2$, which can be the same or different, are H, CH$_3$, C$_2$H$_5$, C$_3$H$_7$, OCH$_3$, NH$_2$, CN, CF$_3$, CHF$_2$, CH$_2$F or halogen and n is 1 to 4, and a 4(5)-imidazole aldehyde (IIId)

where R′ is as defined before, in an appropriate solvent, e.g. tetrahydrofuran or dimethoxyethane, in the presence of a low valent titanium reagent in an inert atmosphere, e.g. in nitrogen or argon, to give the compounds of formula (Id) where R$_4$ and R$_5$ together form a bond (IVd)

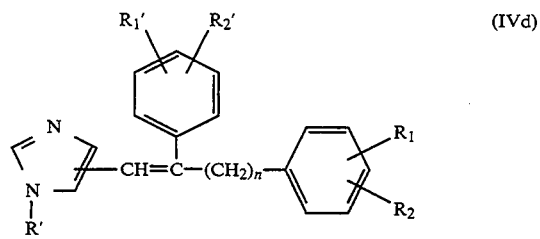

The unsaturated compounds (IVd) are isolated and after that hydrogenated. Alternatively they can be hydrogenated directly in an acidic medium without previous isolation. The hydrogenation is conveniently carried out at room temperature with good stirring in alcohol, e.g. ethanol, in the presence of a catalyst in a hydrogen atmosphere. Suitable catalysts are for example platinum oxide, palladium-on-carbon or Raney-nickel.

The reaction scheme for this step can be illustrated as follows:

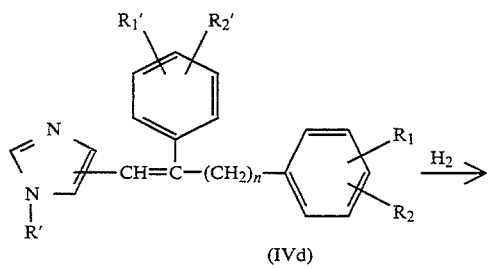

(IVd)

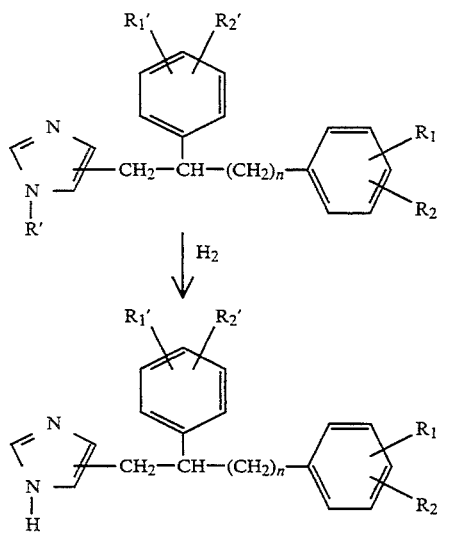

(V)

If R' is a substituted or unsubstituted benzyl, this group may be removed by hydrogenation as well. In this case the hydrogenation is performed in an acidic medium such as hydrochloric acid-ethanol mixture.

The reaction scheme of this hydrogenation which leads to compounds of formula (Id) wherein R', $R_4$ and $R_5$ each are hydrogen can be illustrated as follows:

(Vd)

(VId)

Another method to remove the benzylic R' group is a hydrogen transfer reaction in which the starting compound (Vd) is refluxed with ammonium formate and 10% Pd/C in an appropriate lower alcohol, such as methanol or ethanol, or its aqueous solution. The compounds (VId) can also be prepared from the compounds (IVd) by hydrogen transfer reaction with ammonium formate or by hydrogenating both the double bond and the protecting benzyl group at the same time. If one or more of the substituents $R_1$, $R_2$, $R'_1$ and $R'_2$ is CN, it must be protected during the hydrogen transfer reaction.

The ketone of formula (IId) can be prepared for example from an appropriately substituted acetophenone and benzaldehyde by condensation and hydrogenation.

Another method of preparing compounds of formula (Id) is a reaction which comprises reacting a ketone of formula (VIId)

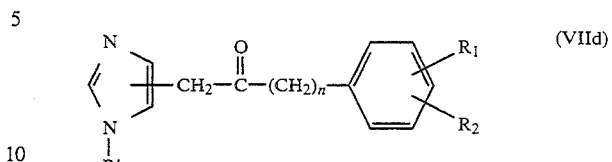
(VIId)

wherein R' and n are as defined before and $R_1$ and $R_2$, which can be the same or different, are H, $CH_3$, $C_2H_5$, $C_3H_7$, $OCH_3$, $NO_2$, $CF_3$, $CHF_2$, $CH_2F$ or halogen, with an appropriate halide derivative of the formula (VIIId)

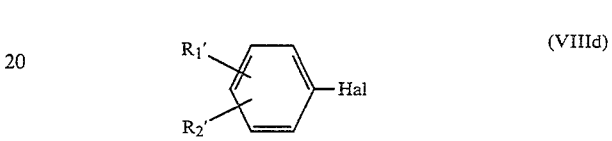
(VIIId)

wherein $R'_1$ and $R'_2$, which can be the same or different, are H, $CH_3$, $C_2H_5$, $C_3H_7$, $OCH_3$, $NO_2$, $CF_3$, $CHF_2$, $CH_2F$ or halogen, in the presence of an alkyl lithium, such as n-butyl lithium, or magnesium in an appropriate solvent, such as tetrahydrofuran, to give compounds of formula (IXd)

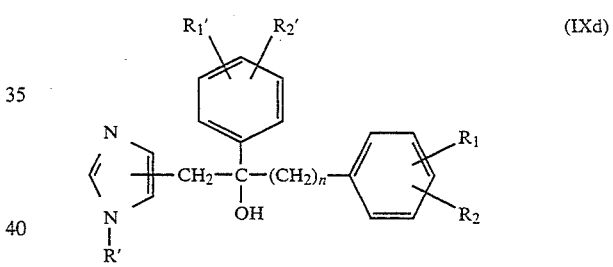
(IXd)

wherein R', $R_1$, $R_2$, $R'_1$, $R'_2$ and n are as defined for formulae (VIId) and (VIIId). Compounds of formula (IXd) are further dehydrated to form compounds of formula (Id) where $R_4$ and $R_5$ together form a bond (IVd). Water is eliminated by usual methods, i.e. by heating with dry potassium hydrogen sulfate. The unsaturated compounds (IVd) are hydrogenated by the methods described before. The benzylic R' can also be removed from the compounds of formula (IXd) by a hydrogen transfer reaction to give compounds of formula (Xd)

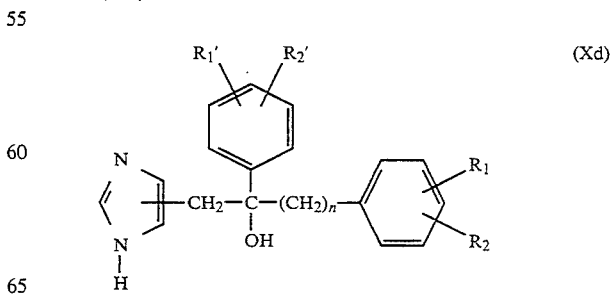
(Xd)

wherein $R_1$, $R_2$, $R'_1$ and $R'_2$ are as defined for formula (IXd).

Compounds of formula (VIId) can be prepared e.g. from a 4(5)-imidazole acetaldehyde and an appropriate arylalkylhalide and then oxidizing.

Compounds of formula (Id) wherein one or more of the substituents are CN can also be prepared by the method described above but then the CN group(s) in the formulae (VIId) and (VIIId) must be protected by a tert-butylaminocarbonyl group or an oxazoline group and R' is a protecting benzyl group. $NO_2$ can not be one of the substituents. Compounds of formula (IXd) wherein one or more of the substituents are a tert-butylaminocarbonyl group or an oxazoline group (IXd') are dehydrated and hydrogenated by the methods described before and further refluxed in $SOCl_2$ to give compounds of formula (VId) wherein one or more of the substituents $R_1$, $R_2$, $R'_1$ and $R'_2$ are CN.

Compounds of formula (Id) wherein one or more of the substituents, $R_2$, $R'_1$ and $R'_2$ are CN can also be prepared by refluxing compounds of formula (IXd) wherein one or more of the substituents are a tert-butylaminocarbonyl group or an oxazoline group (IXd') with e.g. $SOCl_2$, $POCl_3$ or $PCl_5$ optionally in an appropriate solvent, such as acetonitrile, to give compounds of formula (Id) wherein R' is a benzyl group, $R_4$ and $R_5$ form together a bond and one or more of the substituents $R_1$, $R_2$, $R'_1$ and $R'_2$ are CN. The substituents that are not CN are H, $CH_3$, $C_2H_5$, $C_3H_7$, $OCH_3$, $CF_3$, $CHF_2$, $CH_2F$ or halogen. The unsaturated compounds are hydrogenated by the methods described before.

Compounds of formula (Xd) wherein one or more of the substituents are a tert-butylaminocarbonyl or an oxazoline group (Xd') may be dehydrated by e.g. $SOCl_2$, $POCl_3$ or $PCl_5$ as described before to form compounds of formula (XId)

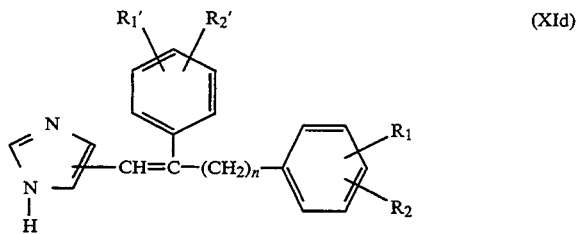

(XId)

wherein one or more of the substituents $R_1$, $R_2$, $R'_1$ and $R'_2$ are CN and the substituents that are not CN are H, $CH_3$, $C_2H_5$, $C_3H_7$, $OCH_3$, $CF_3$, $CHF_2$, $CH_2F$ or halogen.

Another method to give compounds of formula (Id) wherein the substituents are as defined for formula (XId) is refluxing compounds of formula (IXd') or (Xd'), in an appropriate solvent, such as dichloromethane, in the presence of $SOCl_2$ to give compounds of formula (IVd) wherein R' is H or a protecting group and the substituents $R_1$, $R_2$, $R'_1$ and $R'_2$ are as defined for formula (Xd'). The unsaturated compounds are further reacted by a hydrogen transfer reaction or hydrogenated to give compounds of formula (VId) wherein the substituents are as defined for formula (Xd') which are further reacted with e.g. $SOCl_2$ to give compounds of formula (Id) wherein the substituents are as defined for formula (XId).

Compounds of formula (VId) wherein the substituents are as defined for formula (Xd') can be prepared by a hydrogen transfer reaction from compounds of formula (IXd').

The compounds of formula (Id) wherein one or more of the substituents are CN can be prepared from the corresponding compounds where one or more of the substituents $R_1$, $R_2$, $R'_1$ and $R'_2$ are $NH_2$ by diazotization.

Compounds of formula (Id) wherein one or more of the substituents $R_1$, $R_2$, $R'_1$ and $R'_2$ are $NH_2$, can be prepared by hydrogenating the corresponding compounds where one or more of the substituents are $NO_2$. Compounds of formula (Id) wherein one or more of the substituents are $NO_2$ can be prepared by nitration.

Compounds of formula (Id) where R' is a benzyl group can be prepared by benzylating the corresponding compounds where R is hydrogen. The starting compound is first treated with a strong base such as sodium hydroxide in water or sodium hydride in an appropriate solvent e.g. dimethyl formamide, to give the alkali metal salt of the imidazole an then in the second step adding to this benzyl halide. the reaction scheme can be illustrated as follows:

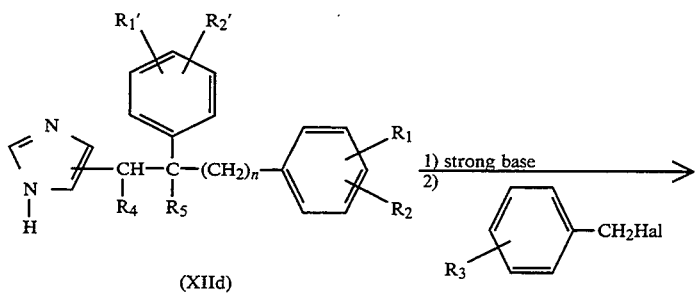

(XIId)

-continued

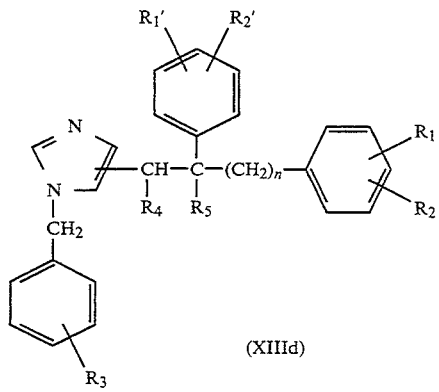

(XIIId)

The free $NH_2$ substituent must be protected during the benzylation reaction.

Another method for the preparation of compounds of formula (IVd) is the reaction of a diphenylhalogen compound (XIVd)

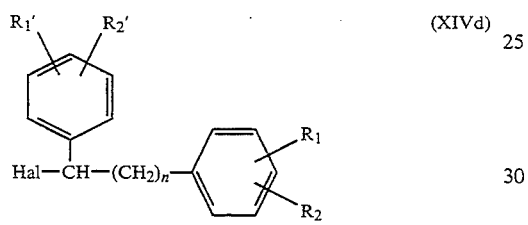

(XIVd)

wherein $R_1$, $R_2$, $R'_1$ and $R'_2$, which can be the same or different, are H, $CH_3$, $C_2H_5$, $C_3H_7$, $OCH_3$, $NO_2$, $CF_3$, $CHF_2$, $CH_2F$ or halogen, n is 1 to 4 and Hal is halogen, with a 4(5)-imidazole aldehyde (IIId) using n-butyllithium as a reagent to give compounds of formula (XVd)

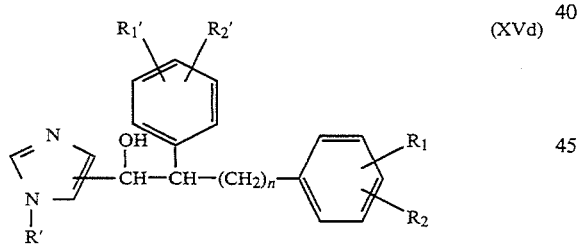

(XVd)

The compounds of formula (XVd) may be dehydrated to give the compounds of formula (IVd) wherein the substituents $R_1$, $R_2$, $R'_1$ and $R'_2$, which can be the same or different, are H, $CH_3$, $C_2H_5$, $C_3H_7$, $OCH_3$, $NO_2$, $CF_3$, $CHF_2$, $CH_2F$ or halogen. The compounds of formula (IVd) wherein one or more of the substituents are CN may be prepared by the same method when the CN-group(s) is (are) protected.

Still another method for preparing of compounds of formula (Id) is a process which comprises a Reformatskii reaction of the 4(5)-imidazole aldehyde (IIId) with an ester of α-bromophenylacetic acid (XVId)

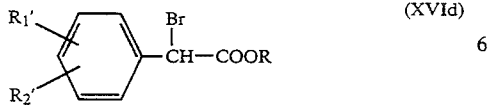

(XVId)

wherein $R'_1$ and $R'_2$, which can be the same or different, are H, $CH_3$, $C_2H_5$, $C_3H_7$, $OCH_3$, $NO_2$, $CF_3$, $CHF_2$, $CH_2F$ or halogen and R is a lower alkyl, to give an ester of β-hydroxy-α-phenylimidazolepropionic acid (XVIId)

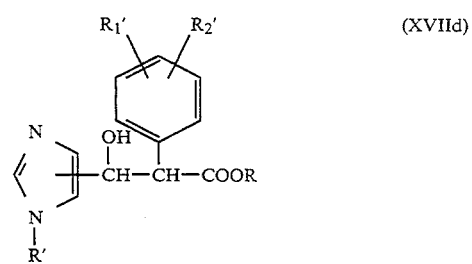

(XVIId)

The compounds of formula (XVIId) can be dehydrated and hydrogenated to give the saturated α-phenylimidazolepropionic acid esters (XVIIId) which can be reduced to aldehydes of formula (XIXd)

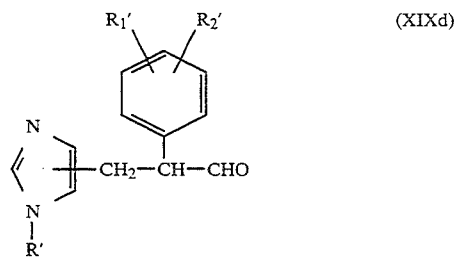

(XIXd)

or converted to amides of formula (XXd)

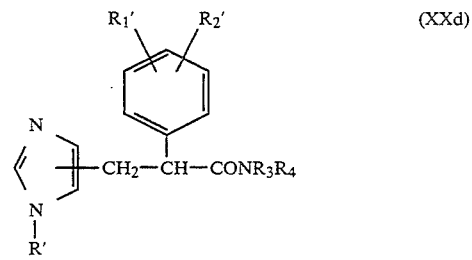

(XXd)

wherein $R_3$ and $R_4$ are lower alkyl or N, $R_3$ and $R_4$ together form a ring. The reaction of the compounds of formula (XIXd) or (XXd) with an appropriate aryl or arylalkyl halide (XXId)

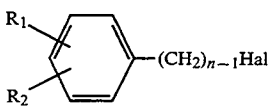

wherein $R_1$ and $R_2$, which can be the same or different, are H, $CH_3$, $C_2H_5$, $C_3H_7$, $OCH_3$, $NO_2$, $NH_2$, CN, $CF_3$, $CHF_2$, $CH_2F$ or halogen and n is 1 to 4, in the presence of alkyl lithium, e.g. n-butyl lithium, or magnesium give alcohols (XXIId) or ketones (XXIIId) respectively. The substituents $R_1$ and $R_2$ of the halide (XXId) must be protected if they are $NH_2$ or CN.

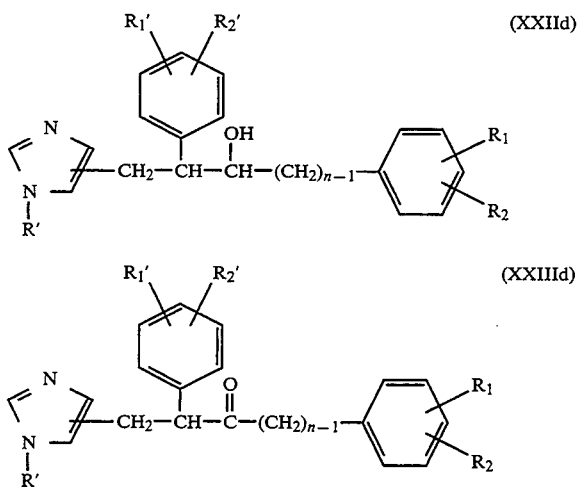

The compounds of formulae (XXIId) and (XXIIId) can further be reduced, dehydrated and hydrogenated to give the compounds of formula (Id) wherein $R_1$, $R_2$, $R'_1$ and $R'_2$, which can be the same or different, are H, $CH_3$, $C_2H_5$, $C_3H_7$, $OCH_3$, $NH_2$, CN, $CF_3$, $CHF_2$, $CH_2F$ or halogen.

The compounds of formula (Ia) and (Ic), their non-toxic, pharmaceutically acceptable acid salts or mixtures thereof may be administered parenterally, intravenously or orally. Typically, an effective amount of the compound is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the derivative is administered, etc., and of course the structure of the compound.

The pharmaceutical carriers which are typically employed with the compounds of the present invention may be solid or liquid and are generally selected with the planned manner of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the compound and the carrier may be fashioned into numerous acceptable forms, such as tablets, capsules, suppositories, solutions, emulsions and powders.

The compounds of the invention are especially valuable as aromatase inhibiting agents and are therefore useful in the treatment of estrogen dependent diseases, e.g. breast cancer or benign prostatic hyperplasia (BPH).

Estrogens are essential steroids in the physiology and function of normal development of breast and sex organs in women. On the other hand estrogens are known to stimulate the growth of estrogen dependent cancers, especially breast and endometrial cancers, and they may increase the risk of development of breast cancer if given at pharmacological doses for a long time. Excessive production of estradiol may also cause other, benign disorders in hormone dependent organs. The importance of estrogens as cancer growth stimulators and/or regulators is clearly stressed by the fact that anti-estrogens have reached a central position in the treatment of estrogen receptor rich breast cancers. Antiestrogens act by binding to estrogen receptors and thereby inhibiting the biological effects of estrogens. Another approach for blocking estrogen effect is to inhibit the synthesis of estrogens. This has been achieved clinically by the unspecific steroid synthesis inhibitor aminoglutethimide. The estrogen synthesis could be blocked specifically by inhibiting the enzyme aromatase, which is the key enzyme in biochemical estrogen synthesis pathway. Aromatase inhibition is important because several breast tumors synthesize estradiol and estrone in situ and exhibit therefore continuous growth stimulation (Alan Lipton et al., Cancer 59:779–782, 1987).

The ability of the compounds of the invention to inhibit the enzyme aromatase has been tested by in vitro assay according to M. Pasanen (Biological Research in Pregnancy, vol. 6, No. 2, 1985, pp. 94–99). Human aromatase enzyme was used. The enzyme was prepared from human placenta, which is rich of the enzyme. Microsomal fraction (100000×g precipitate) was prepared by centrifugation. The enzyme preparation was used without further purification. Test compounds were added together with 100000 dpm of 1,2[$^3$H]-androstene-3,17-dione and NADPH generating system. The concentrations of the test compounds were 0,001; 0,01; 0,1 and 1,0 mM. The incubation was carried out at 37° C. for 40 min. Aromatization of 1,2[$^3$H]-androstene-3,17-dione results in the production of $^3H_2O$. The tritiated water and the tritiated substrate are easily separated by a Sep-Pak® minicolumn, which absorbs the steroid but allows free water elution. Radioactivity was counted by a liquid scintillation counter. Aromarase inhibition was evaluated by comparing the $^3H_2O$-radioactivity of inhibitor treated samples to controls containing no inhibitor. IC-50 values were calculated as concentrations which inhibited the enzyme activity 50%. These concentrations are presented in Table 2.

Cholesterol side chain cleavage (CSCC) activity (desmolase) was measured according to the method of Pasanen and Pelkonen (Steroids 43:517–527, 1984). Incubations were carried out in 1,5 ml Eppendorf plastic tubes, and an Eppendorf shaker, centrifuge and incubator were used as a unit. In a 300 μl incubation volume, the substrate (5 μM) was prepared according to Hanukoglu and Jefcoate (J. Chromatogr. 190:256–262, 1980), and 100000 dpm of radioactive $^3$H-4-cholesterol (the purity of the compound was checked by TLC) in 0,5% Tween 20, 10 mM $MgCl_2$, 5 μM cyanoketone and 2 mM NADPH was added. Controls contained all the above substances but the enzyme preparation was inactivated prior to the incubation by the addition of 900 μl of methanol. The mitochondrial fraction (1 mg protein)

from human placenta or bovine adrenals was used as a source of enzyme. After 30 min incubation at 37° C., the reaction was terminated by the addition of 900 μl of methanol; 1500 dpm of marker $^{14}$C-4-pregnenolone was added to each incubate and the tubes were vigorously shaken. After 10 min equilibration, the methanol-precipitated proteins were separated by centrifugation (8000×g for 2 min) and the supernatant was sucked into 1 ml plastic injection syringe and loaded onto the pre-equilibrated (75% methanol) minicolumn. The column was washed with one ml of 75% methanol and then with 3 ml of 80% methanol. The 80% methanol eluate was run into the counting vial and 10 ml of scintillation liquid was added. Radioactivity was counted using a double-label program on a liquid scintillation counter (LKB RackBeta). Typical activities for placental and bovine adrenal enzyme preparation were 0,5–3 and 50–100 pmol pregnenolone formed/mg protein/min, respectively.

In inhibition experiments, the substance (final concentration range from 1 to 1000 μM) was added into incubation mixture in a volume of 10–20 μl, usually as methanol or ethanol solution. The same volume of the solute was added into control incubation vial. The IC-50 values (concentration causing a 50% inhibition) were determined graphically and are presented in Table 2.

TABLE 1

| No. | Compounds tested Name |
|---|---|
| 1a. | 4-[4-(4-methylphenyl)-4-phenylbutyl]-1H-imidazole |
| 2a. | 1-benzyl-5-[4-(4-methylphenyl)-4-phenylbutyl]-1H-imidazole |
| 3a. | 1-benzyl-5-[4-(3-methylphenyl)-4-phenylbutyl]-1H-imidazole |
| 4a. | 4-(4-(3-methylphenyl)-4-phenylbutyl]-1H-imidazole |
| 5a. | 4-[4-(2-methylphenyl)-4-phenylbutyl]-1H-imidazole |
| 6a. | 1-benzyl-5-[4-(2-methylphenyl)-4-phenylbutyl]-1H-imidazole |
| 7a. | 1-benzyl-5-(4,5-diphenylpentyl)-1H-imidazole |
| 8a. | 4-(4,5-diphenylpentyl)-1H-imidazole |
| 9a. | 4-(4,4-diphenylbutyl)-1H-imidazole |
| 10a. | 1-benzyl-5-(4,4-diphenylbutyl)-1H-imidazole |
| 11a. | 4-(4-methoxyphenyl)-4-phenylbutyl]-1H-imidazole |
| 12a. | 4-[4,4-bis(4-methoxyphenyl)butyl]-1H-imidazole |
| 13a. | 4-[4,4-bis(3-methylphenyl)butyl]-1H-imidazole |
| 14a. | 4-[4-(3,5-dimethylphenyl)-4-phenylbutyl]-1H-imidazole |
| 15a. | 4-[4-(3,4-dimethylphenyl)-4-phenylbutyl]-1H-imidazole |
| 16a. | 4-[4-(3,5-dimethylphenyl)-4-(3-methylphenyl)butyl]-1H-imidazole |
| 17a. | 4-[4,4-bis(4-methylphenyl)butyl]-1H-imidazole |
| 18a. | 4-(5,5-diphenylpentyl)-1H-imidazole |
| 19a. | 4-(6,6-diphenylhexyl)-1H-imidazole |
| 20a. | 4-[4-(2-fluorophenyl)-4-phenylbutyl]-1H-imidazole |
| 21a. | 4-[4-(4-fluorophenyl)-4-phenylbutyl]-1H-imidazole |
| 22a. | 4-(4,4-diphenyl-1-butenyl)-1H-imidazole |
| 23a. | 4-[4,4-bis(4-fluorophenyl)butyl]-1H-imidazole |
| 24a. | 4-[4,4-bis(4-nitrophenyl)butyl]-1H-imidazole |
| 25a. | 4-[4,4-bis(4-aminophenyl)butyl]-1H-imidazole |
| 26a. | 4-[4-(4-ethylphenyl)-4-phenylbutyl]-1H-imidazole |
| 1c | 4-[1-(4-fluorophenyl)-5-phenylpentyl]-1H-imidazole |
| 2c | 4-[1-(4-fluorophenyl)-5-(2-methylphenyl)pentyl]-1H-imidazole |
| 3c | 4-[1-(4-fluorophenyl)-5-(3-methylphenyl)pentyl]-1H-imidazole |
| 4c | 4-[1-(4-fluorophenyl)-5-(4-methylphenyl)pentyl]-1H-imidazole |
| 5c | 4-[5-(3,5-dimethylphenyl)-1-(4-fluorophenyl)pentyl]-1H-imidazole |
| 6c | 4-(1,5-diphenylpentyl)-1H-imidazole |
| 7c | 4-(1,3-diphenylpropyl)-1H-imidazole |
| 8c | 1-benzyl-5-(1,3-diphenylpropyl)-1H-imidazole |
| 9c | 4-[1-(4-fluorophenyl)-3-phenylpropyl]-1H-imidazole |
| 10c | 4-[1-(4-fluorophenyl)-4-phenylbutyl]-1H-imidazole |

TABLE 1-continued

| No. | Compounds tested Name |
|---|---|
| 11c | 4-[1-(4-fluorophenyl)-5-(3-methoxyphenyl)pentyl]-1H-imidazole |
| 12c | 4-[1-(4-fluorophenyl)-5-(4-methoxyphenyl)pentyl]-1H-imidazole |
| 13c | 4-[1-(4-fluorophenyl)-5-(2,6-dimethylphenyl)pentyl]-1H-imidazole |
| 14c. | 4-[1,3-bis(4-fluorophenyl)propyl]-1H-imidazole |
| 15c. | 4-[1,4-bis(4-fluorophenyl)butyl]-1H-imidazole |
| 16c. | 4-(2,4-diphenylbutyl)-1H-imidazole |
| 17c. | 4-[2-(4-fluorophenyl)-4-phenylbutyl]-1H-imidazole |
| 18c. | 4-[2,4-bis(4-fluorophenyl)butyl]-1H-imidazole |
| 19c. | 4-[2-(4-cyanophenyl)-4-(4-fluorophenyl)butyl]-1H-imidazole |

TABLE 2

Inhibition of human aromatase and desmolase (CSCC) by test compounds. IC-50 represents the concentration which inhibits the enzyme 50%.

| COMPOUND NO: | IC-50 μmol/l | IC-50 CSCC μmol/l |
|---|---|---|
| 1a | 2,9 | 96 |
| 2a | 19 | 50 |
| 3a | 13 | 38 |
| 4a | 2,5 | 7,5 |
| 5a | 3,4 | 29 |
| 6a | 8,5 | 32 |
| 7a | 15 | |
| 8a | 4,7 | 27 |
| 9a | 2 | 320 |
| 10a | 7 | |
| 11a | 3,5 | 190 |
| 12a | 10 | 46 |
| 13a | 28 | 48 |
| 14a | 7,5 | 65 |
| 15a | 5,0 | 39 |
| 16a | 125 | 95 |
| 17a | 3,5 | 110 |
| 18a | 1,7 | 68 |
| 19a | 14,5 | 61 |
| 20a | 16 | 38 |
| 21a | 2,8 | 80 |
| 22a | 8,5 | 165 |
| 23a | 3,3 | 175 |
| 24a | 20 | 37 |
| 25a | 26 | 210 |
| 26a | 8,5 | 65 |
| 1c | 2,8 | 19 |
| 2c | 3,5 | 16 |
| 3c | 3,8 | 57 |
| 4c | 8,5 | 170 |
| 5c | 7,5 | 80 |
| 6c | 25 | — |
| 7c | 4,5 | 7,5 |
| 8c | 30 | — |
| 9c | 0,72 | 22 |
| 10c | 0,75 | 31 |
| 11c | 2,6 | 12 |
| 12c | 3 | 22,5 |
| 13c | 7,7 | 31 |
| 14c | 2,2 | 22 |
| 15c | 0,63 | 29 |
| 16c | 5,5 | 12 |
| 17c | 2,2 | 28 |
| 18c | 1,3 | 20 |
| 19c | 0,5 | 6,6 |

The anti-tumour effect was investigated in vivo against DMBA-induced rat mammary adenocarcinomas by the following method. Mammary adenocarcinoma was induced with DMBA in 50±2 days old female rats. Treatment with the compound under test was started after palpable tumours had appeared. Tumour size and amount of tumours were evaluated once a week. Tumour sizes in the control group, treated with solvent, were compared with the test groups. Daily administration schedule was employed for five weeks and animals were sacrificed. The change in tumour sizes was evaluated.

Results were evaluated as changes in the sizes of tumours and divided into three groups, namely increasing, stable and decreasing sizes of tumours. The anti-tumour effect of 4-(4,4-diphenylbutyl)-1H-imidazole (compound 9a in Table 2) was tested and the results are presented in Table 3.

TABLE 3

Number of different tumour types in control and 4-(4,4-diphenylbutyl)-1H-imidazole treated groups of DMBA-induced mammary tumour rats.

| Group | decreasing | stable | increasing |
|---|---|---|---|
| control | 3 | 21 | 42 |
| 4-(4,4-diphenyl-butyl)-1H-imidazole 3 mg/kg | 2 | 14 | 37 |
| 4-(4,4-diphenyl-butyl)-1H-imidazole 30 mg/kg | 21 | 3 | 15 |

Acute toxicity, $LD_{50}$, was determined by using young adult female mice of NMRI-Strain. The administration of the test compounds was oral. The $LD_{50}$ values of the test compounds of formula (Ia) were 350 mg/kg or more and of formula (Ic) 400 mg/kg or more.

The daily dose for a patent varies from about 20 to 200 mg, administered orally.

The following examples illustrate the invention.

$^1$H NMR spectra were determined with a Bruker WP 80 DS, apparatus (80 MHz) in the case of compounds 1a-26a and 1c-15c and a Bruker AC-P300 apparatus in the case of compounds 16c-19c. The reference substance was tetramethylsilane. MS spectra were determined with Kratos MS80RF Autoconsole apparatus.

EXAMPLE 1

4-(4,4-diphenylbutyl)-1H-imidazole a) 1-benzyl-5-(1-hydroxy-4,4-diphenylbutyl)-1H-imidazole 2,0 g of magnesium turnings are covered with 60 ml of dry tetrahydrofuran. To the mixture is then added dropwise a solution of 1-bromo-3,3-diphenylpropane (22,9 g) in 20 ml of dry tetrahydrofuran at such a rate that a smooth reaction is maintained. After the addition is complete, the reaction mixture is refluxed for one additional hour and cooled to room temperature. The reaction mixture is then added dropwise to a solution of 1-benzyl-5-imidazolecarbaldehyde (7,35 g) in 80 ml of tetrahydrofuran at 60° C. After the addition is complete, the reaction mixture is refluxed for 2 hours, cooled and poured into cold water. Tetrahydrofuran is evaporated and to the solution is added conc. hydrochloric acid. The solution is cooled and the precipitate which contains the product as hydrochloride salt is removed by filtration, washed with water and dried. Yield 14,1 g. M.p. 160°–168° C.

$^1$H NMR (as HCl-salt, MeOH-d$_4$): 1.50–2.30 (m, 4H), 3.82 (t, 1H), 4.65 (t, 1H), 5.43 (s, 2H), 7.05–7.50 (m, 16H), 8.62 (d, 1H)

Using the same method for example the following compounds included in the invention were prepared:

1-benzyl-5-[1-hydroxy-4-(2-methylphenyl)-4-phenyl-butyl]-1H-imidazole $^1$H NMR (as HCl-salt, MeOH-d$_4$): 1.50–2.40 (m, 4H), 2.21 and 2.15 (2s, 3H), 4.07 (t, 1H), 4.70 (m, 1H), 5.49 and 5.46 (2s, 2H), 6.80–7.50 (m, 15H), 8.88 (s, 1H)

1-benzyl-5-[1-hydroxy-4-(3-methylphenyl)-4-phenyl-butyl]-1H-imidazole $^1$H NMR (as HCl-salt, CDCl$_3$): 1.35–2.35 (m, 4H), 2.26 (s, 3H), 3.73 (t, 1H), 4.62 (m, 1H), 5.38 (s, 2H), 6.80–7.40 (m, 15H), 8.51 (s, 1H)

1-benzyl-5-[1-hydroxy-4-(4-methylphenyl)-4-phenyl-butyl]-1H-imidazole $^1$H NMR (as HCl-salt, CDCl$_3$): 1.40–2.40 (m, 4H), 2.23 and 2.24 (2s, 3H), 3.74 (t, 1H), 4.65 (broad t, 2H), 5.38 (s, 2H), 6.80–7.40 (m, 15H), 8.55 (s, 1H)

1-benzyl-5-[1-hydroxy-4,4-bis(4-methylphenyl)-butyl]-1H-imidazole. M.p. of hydrochloride 155°–158° C.

1-benzyl-5-(1-hydroxy-4,5-diphenylpentyl)-1H-imidazole $^1$H NMR (as hydrogen sulphate salt, MeOH-d$_4$): 1.35–1.90 (m, 4H), 2.82 (broad s, 3H), 4.54 (t, 1H), 5.42 (s, 2H), 6.85–7.50 (m, 16H), 8.80 (s, 1H)

1-benzyl-5-[1-hydroxy-4-(4-methoxyphenyl)-4-phenyl-butyl]-1H-imidazole $^1$H NMR (as HCl-salt, MeOH-d$_4$): 1.50–2.30 (m, 4H), 3.70 (s, 3H), 3.79 (t, 1H), 4.69 (t, 1H), 5.46 (s, 2H), 6.79 (d, 2H), 7.0–7.55 (m, 13H), 8.85 (d, 1H)

1-benzyl-5-[1-hydroxy-4,4-bis(4-methoxyphenyl)butyl]-1H-imidazole $^1$H NMR (as base, MeOH-d$_4$): 1.50–2.20 (m, 4H), 3.66 (t, 1H), 3.74 (s, 6H), 4.50 (t, 1H), 5.24 (s, 2H), 6.70–7.60 (m, 15H)

1-benzyl-5-[4-(2-fluorophenyl)-1-hydroxy-4-phenyl-butyl]-1H-imidazole. M.p. of hydrochloride 160°–163° C.

$^1$H NMR (as HCl-salt, CDCl$_3$): 1.45–2.45 (m, 4H), 4.17 (t, 1H), 4.67 (t, 1H), 5.43 (s, 2H), 6.80–7.50 (m, 15H), 8.43 (s, 1H)

1-benzyl-5-[4-(4-fluorophenyl)-1-hydroxy-4-phenyl-butyl]-1H-imidazole. M.p. of hydrochloride 168°–171° C.

$^1$H NMR (as HCl-salt, MeOH-d$_4$): 1.50–2.30 (m, 4H), 3.84 (t, 1H), 4.68 (t, 1H), 5.49 (s, 2H), 6.80–7.55 (m, 15H), 8.87 (d, 1H)

1-benzyl-5-(1-hydroxy-5,5-diphenylpentyl)-1H-imidazole $^1$H NMR (as base, CDCl$_3$): 1.2–2.2 (m, 6H), 3.70 (t, 1H), 4.54 (t, 1H), 5.46 (s, 2H), 6.8–7.3 (m, 16H), 8.58 (s, 1H)

1-benzyl-5-(1-hydroxy-6,6-diphenylhexyl)-1H-imidazole. M.p. of hydrochloride 147°–149° C.

$^1$H NMR (as HCl-salt, MeOH-d$_4$): 1.6–2.2 (m, 8H), 3.85 (t, 1H), 4.60 (t, 1H), 5.53 (s, 2H), 7.0–7.4 (m, 15H), 7.47 (s, 1H), 8.90 (s, 1H)

1-benzyl-5-[4-(4-ethylphenyl)-1-hydroxy-4-phenyl-butyl]-1H-imidazole $^1$H NMR (as HCl-salt, MeOH-d$_4$): 1.71 (t, 3H), 1.50–2.35 (m, 4H), 2.57 (q, 2H), 3.78 (t, 1H), 4.68 (t, 1H), 5.46 (s, 2H), 6.9–7.5 (m, 15H), 8.82 (d, 1H)

1-benzyl-5-[4,4-bis(4-fluorophenyl)-1-hydroxybutyl]-1H-imidazole $^1$H NMR (as HCl-salt, MeOH-d$_4$): 1.50–2.00 (m, 4H), 3.86 (t, 1H), 4.70 (t, 1H), 5.52 (s, 2H), 6.80–7.50 (m, 14H), 8.89 (d, 1H)

b) 1-benzyl-5-(4,4-diphenyl-1-butenyl)-1H-imidazole 1-benzyl-5-(1-hydroxy-4,4-diphenylbutyl)-1H-imidazole hydrochloride (5,0 g) and 30,0 g of anhydrous potassium hydrogen sulphate are heated at 150° C. for 4 hours. The mixture is cooled, 90 ml of ethanol is added to dissolve the product. The mixture is then filtered and the filtrate is evaporated to minor volume. Water is added and the mixture is made alkaline with sodium hydroxide. The product is extracted in methylene chloride, washed with water and evaporated to dryness. The product is then made to hydrochloride salt with dry hydrochloric acid in dry ethylacetate. Yield is 2,9 g. M.p. 204°–206° C.

$^1$H NMR (as HCl-salt, MeOH-d$_4$): 2.88–3.05 (m, 2H), 4.08 (t, 1H), 5.29 (s, 2H), 6.22–6.32 (m, 2H), 7.00–7.50 (m, 16H), 8.87 (d, 1H)

Using the same method for example the following compounds included in the invention were prepared:

1-benzyl-5-[4,4-bis(3-methylphenyl)-1-butenyl]-1H-imidazole. M.p. of hydrochloride 152°–156° C.

$^1$H NMR (as HCl-salt, MeOH-d$_4$): 2.26 (s, 6H), 2.85–3.05 (m, 2H), 3.99 (t, 1H), 5.27 (s, 2H), 6.21–6.31 (m, 2H), 6.80–7.50 (m, 14H), 8.86 (d, 1H)

1-benzyl-5-[4-(3,5-dimethylphenyl)-4-(3-methylphenyl)-1-butenyl]-1H-imidazole $^1$H NMR (as HCl-salt, MeOH-d$_4$): 2.22 (s, 3H), 2.23 (s, 3H), 2.26 (s, 3H), 2.85–3.05 (m, 2H), 3.94 (t, 1H), 5.26 (s, 2H), 6.20–6.30 (m, 2H), 6.75–7.50 (m, 13H), 8.84 (d, 1H)

1-benzyl-5-[4-(3,5-dimethylphenyl)-4-phenyl-1-butenyl]-1H-imidazole. M.p. 110°–112° C.

$^1$H NMR (as HCl-salt, MeOH-d$_4$): 2.22 (s, 6H), 2.85–3.05 (m, 2H), 3.98 (t, 1H), 5.27 (s, 2H), 6.20–6.30 (m, 2H), 6.75–7.5 (m, 14H), 8.87 (d, 1H)

1-benzyl-5-[4-(2-methylphenyl)-4-phenyl-1-butenyl]-1H-imidazole $^1$H NMR (as hydrogen sulphate, MeOH-d$_4$): 2.19 (s, 3H), 2.80–3.05 (m, 2H), 4.28 (t, 1H), 5.29 (s, 2H), 6.0–6.60 (m, 2H), 7.0–7.5 (m, 14H), 7.52 (d, 1H), 8.85 (d, 1H)

1-benzyl-5-[4-(3-methylphenyl)-4-phenyl-1-butenyl]-1H-imidazole $^1$H NMR (as base, CDCl$_3$): 2.27 (s, 3H), 2.75–3.95 (m, 2H), 3.93 (t, 1H), 4.89 (s, 2H), 5.70–6.10 (m, 2H), 6.80–7.40 (m, 16H)

1-benzyl-5-[4-(4-methylphenyl)-4-phenyl-1-butenyl]-1H-imidazole $^1$H NMR (as base, CDCl$_3$): 2.27 (s, 3H), 2.70–2.95 (m, 2H), 3.93 (t, 1H), 4.89 (s, 2H), 5.60–6,20 (m, 2H), 6.80–7.50 (m, 16H)

1-benzyl-5-[4,4-bis(4-methylphenyl)-1-butenyl]-1H-imidazole. M.p. of hydrochloride 128°–132° C.

1-benzyl-5-[4-(4-methoxyphenyl)-4-phenyl-1-butenyl]-1H-imidazole $^1$H NMR (as HCl-salt, CDCl$_3$): 2.70–2.95 (m, 2H), 3.95 (t, 1H), 5.16 (s, 2H), 5.70–6.20 (m, 2H), 6.70–7.40 (m, 15H), 8.99 (s, 1H)

1-benzyl-5-[4,4-bis(4-methoxyphenyl)-1-butenyl]-1H-imidazole $^1$H NMR (as base, CDCl$_3$): 2.60–2.90 (m, 2H), 3.74 (s, 6H), 3.78 (t, 1H), 4.92 (s, 2H), 5.80–6.00 (m, 2H), 6.65–7.50 (m, 15H)

1-benzyl-5-(4,5-diphenyl-1-pentenyl)-1H-imidazole $^1$H NMR (as base, CDCl$_3$): 2.30–2.55 (m, 2H), 2.88 (m, 3H), 4.93 (s, 2H), 5.5–6.1 (m, 2H), 6.8–7.5 (m, 17H)

1-benzyl-5-[4-(2-fluorophenyl)-4-phenyl-1-butenyl]-1H-imidazole. M.p. of hydrochloride 195°–201° C.

$^1$H NMR (as base, CDCl$_3$): 2.75–3.00 (m, 2H), 4.34 (t, 1H), 5.97 (s, 2H), 5.80–6.10 (m, 2H), 6.75–7.50 (m, 16H)

1-benzyl-5-[4-(4-fluorophenyl)-4-phenyl-1-butenyl]-1H-imidazole $^1$H NMR (as base, CDCl$_3$): 2.60–2.95 (m, 2H), 3.96 (t, 1H), 4.93 (s, 2H), 5.80–6.05 (m, 2H), 6.75–7.50 (m, 16H)

1-benzyl-5-(6,6-diphenyl-1-hexenyl)-1H-imidazole. M.p. of hydrochloride 184°–186° C.

1-benzyl-5-[4-(4-ethylphenyl)-4-phenyl-1-butenyl]-1H-imidazole $^1$H NMR (as HCl-salt, MeOH-d$_4$): 1.17 (t, 3H), 2.56 (q, 2H), 2.93–2.98 (m, 2H), 4.03 (t, 1H), 5.28 (s, 2H), 6.20–6.34 (m, 2H), 7.08–7.41 (m, 14H), 7.52 (d, 1H), 8.87 (d, 1H)

1-benzyl-5-[4,4-bis(4-fluorophenyl)-1-butenyl]-1H-imidazole $^1$HNMR (as HCl-salt, CDCl$_3$): 2.78–2.94 (m, 2H), 4.01 (t, 1H), 5.27 (s, 2H), 5.82–6.34 (m, 2H), 6.83–7.40 (m, 14H), 9.21 (d, 1H)

c) 1-benzyl-5-(4,4-diphenylbutyl)-1H-imidazole 1-benzyl-5-(4,4-diphenyl-1-butenyl)-1H-imidazole hydrochloride (2,0 g) is dissolved in ethanol and a catalytic amount of Pd/C (10%) is added. The reaction mixture is agitated vigorously at room temperature in a hydrogen atmosphere until the uptake of hydrogen ceases. The mixture is filtered and the filtrate is evaporated to dryness. The residue which is the product is purified by flash chromatography eluting with methylene chloride-methanol mixture. Yield 1,3 g. M.p. of the hydrochloride salt is 200°–202° C.

$^1$H NMR (as HCl-salt, MeOH-d$_4$): 1.30–1.70 (m, 2H), 1.85–2.20 (m, 2H), 2.61 (t, 2H), 3.83 (t, 1H), 5.35 (s, 2H), 7.05–7.50 (m, 16H), 8.89 (d, 1H)

Using the same method for example the following compounds included in the invention were prepared:

1-benzyl-5-[4-(2-methylphenyl)-4-phenylbutyl]-1H-imidazole. Mp. of hydrochloride 200°–205° C.

$^1$H NMR (as HCl-salt, CDCl$_3$): 1.30–1.80 (m, 2H), 1.80–2.15 (m, 2H), 2.22 (s, 3H), 2.48 (t, 2H), 4.02 (t, 1H), 5.31 (s, 2H), 6.96 (s, 1H), 7.0–7.5 (m, 14H), 9.28 (s, 1H)

1-benzyl-5-[4-(3-methylphenyl)-4-phenylbutyl]-1H-imidazole. M.p. of hydrochloride 148–158° C.

$^1$H NMR (as HCl-salt, CDCl$_3$): 1.30–1.80 (m, 2H), 1.80–2.25 (m, 2H), 2.30 (s, 3H), 2.49 (t, 2H), 3.78 (t, 1H), 5.29 (s, 2H), 6.90–7.50 (m, 15H), 9.24 (s, 1H)

1-benzyl-5-[4-(4-methylphenyl)-4-phenylbutyl]-1H-imidazole. M.p. of hydrochloride 164°–170° C.

$^1$H NMR (as HCl-salt, CDCl$_3$): 1.25–1.75 (m, 2H), 1.80–2.25 (m, 2H), 2.29 (s, 3H), 2.48 (t, 2H), 3.78 (t, 1H), 5.31 (s, 2H), 6.80–7.50 (m, 15H), 9.35 (s, 1H)

1-benzyl-5-(4,5-diphenylpentyl)-1H-imidazole. M.p. of hydrochloride 166°–170° C.

$^1$H NMR (as HCl-salt, MeOH-d$_4$): 1.15–1.90 (m, 4H), 2.49 (t, 2H), 2.81 (m, 3H), 5.30 (s, 2H), 6.9–7.50 (m, 16H), 8.82 (s, 1H)

1-benzyl-5-[4-(4-methoxyphenyl)-4-phenylbutyl]-1H-imidazole. M.p. of hydrochloride 180°–187° C.

$^1$H NMR (as HCl-salt, MeOH-d$_4$): 1.25–1.70 (m, 2H), 1.85–2.20 (m, 2H), 2.62 (t, 2H), 3.74 (s, 3H), 3.78 (t, 1H), 5.34 (s, 2H), 6.81 (d, 2H), 7.0–7.5 (m, 13H), 8.84 (d, 1H)

1-benzyl-5-[4-(2-fluorophenyl)-4-phenylbutyl]-1H-imidazole. M.p. of hydrochloride 185°–196° C.

$^1$H NMR (as HCl-salt, MeOH-d$_4$): 1.25–1.75 (m, 2H), 1.80–2.25 (m, 2H), 2.65 (t, 2H), 4.18 (t, 1H), 5.37 (s, 2H), 6.80–7.5 (m, 15H), 8.89 (d, 1H)

1-benzyl-5-[4-(4-fluorophenyl)-4-phenylbutyl]-1H-imidazole. M.p. of hydrochloride 172°–174° C.

$^1$H NMR (as HCl-salt, MeOH-d$_4$): 1.25–1.70 (m, 2H), 1.80–2.25 (m, 2H), 2.64 (t, 2H), 3.85 (t, 1H), 5.37 (s, 2H), 6.80–7.50 (m, 15H), 8.90 (d, 1H)

1-benzyl-5-(5,5-diphenylpentyl)-1H-imidazole $^1$H NMR (as base, MeOH-d$_4$): 1.1–1.6 (m, 4H), 1.8–2.1 (m, 2H), 2.37 (t, 2H), 3.72 (t, 1H), 5.11 (s, 2H), 6.67 (s, 1H), 6.9–7.3 (m, 15H), 7.59 (s, 1H)

1-benzyl-5-[4-(4-ethylphenyl)-4-phenylbutyl]-1H-imidazole $^1$H NMR (as HCl-salt, MeOH-d$_4$): 1.17 (t, 3H), 1.40–1.70 (m, 2H), 1.90–2.20 (m, 2H), 2.57 (q, 2H), 3.80 (t, 1H), 5.34 (s, 2H), 7.00–7.50 (m, 15 H), 8.87 (d, 1H)

1-benzyl-5-[4,4-bis(4-fluorophenyl)butyl]-1H-imidazole $^1$H NMR (as HCl-salt, MeOH-d$_4$): 1.30–1.70 (m, 2H), 1.80–2.25 (m, 2H), 2.64 (t, 2H), 3.87 (t, 1H), 5.40 (s, 2H), 6.80–7.50 (m, 14 H), 8.92 (d, 1H)

d) 4-(4,4-diphenylbutyl)-1H-imidazole 1-benzyl-5-(4,4-diphenylbutyl)-1H-imidazole hydrochloride (0,6 g) is hydrogenated in the mixture of 20 ml of 2N hydrochloric acid and 10 ml of ethanol at 80° C. Pd/C (10%) as catalyst. When the uptake of the hydrogen ceases, the reaction mixture is cooled, filtered and evaporated to dryness. Water is added and the mixture is made alkaline with sodium hydroxide. The product is then extracted to methylene chloride which is washed with water, dried with sodium sulphate and evaporated to dryness. The residue is the product as base and it is made to its hydrochloride in ethyl acetate using dry hydrochloric acid. Yield 0,2 g. M.p. 204°–206° C.

$^1$H NMR (as HCl-salt, MeOH-d$_4$): 1.40–1.90 (m, 2H), 1.90–2.30 (m, 2H), 2.75 (t, 2H), 3.95 (t, 1H), 7.00.–7.40 (m, 11H), 8.72 (d, 1H)

Using the same method for example the following compounds included in the invention were prepared:

4-[4,4-bis(3-methylphenyl)butyl]-1H-imidazole. M.p. of hydrochloride 122°–129° C.

$^1$H NMR (as HCl-salt, MeOH-d$_4$): 1.40–1.90 (m, 2H), 1.90–2.30 (m, 2H), 2.26 (s, 6H), 2.73 (t, 2H), 3.85 (t, 1H), 6.80–7.25 (m, 9H), 8.73 (d, 1H)

4-[4-(3,5-dimethylphenyl)-4-(3-methylphenyl)butyl]-1H-imidazole. M.p. of hydrochloride 75°–82° C.

$^1$H NMR (as HCl-salt, MeOH-d$_4$): 1.40–1.90 (m, 2H), 1.90–2.30 (m, 2H), 2.22 (s, 3H), 2.23 (s, 3H), 2.27 (s, 3H), 2.74 (t, 2H), 3.81 (t, 1H), 6.75–7.30 (m, 8H), 8.72 (d, 1H)

4-[4-(3,5-dimethylphenyl)-4-phenylbutyl]-1H-imidazole. M.p. of hydrochloride 104°–106° C.

$^1$H NMR (HCl-salt, MeOH-d$_4$): 1.40–1.90 (m, 2H), 1.90–2.30 (m, 2H), 2.23 (s, 6H), 2.74 (t, 2H), 3.85 (t, 1H), 6.84 (m, 3H), 7.22 (m, 6H), 8.72 (d, 1H)

4-[4-(3,4-dimethylphenyl)-4-phenylbutyl]-1H-imidazole. M.p. of hydrochloride 118°–121° C.

4-[4-(2-methylphenyl)-4-phenylbutyl]-1H-imidazole. M.p. of hydrochloride 151°–154,5° C.

$^1$H NMR (as HCl-salt, CDCl$_3$): 1.50–2.20 (m, 4H), 2.22 (s, 3H), 2.71 (t, 2H), 4.09 (t, 1H), 6.81 (s, 1H), 7.0–7.4 (m, 9H), 9.04 (s, 1H)

5-[4-(3-methylphenyl)-4-phenylbutyl]-1H-imidazole. M.p. of hydrochloride 140°–153° C.

$^1$H NMR (as HCl-salt, MeOH-d$_4$): 1.40–1.85 (m, 2H), 1.85–2.25 (m, 2H), 2.27 (s, 3H), 2.74 (t, 2H), 3.90 (t, 1H), 6.80–7.30 (m, 10H), 8.69 (d, 1H)

4-[4-(4-methylphenyl)-4-phenylbutyl]-1H-imidazole. M.p. of hydrochloride 173°–177° C.

$^1$H NMR (as HCl-salt, CDCl$_3$+2 drops of MeOH-d$_4$): 1.40–1.80 (m, 2H), 1.80–2.25 (m, 2H), 2.28 (s, 3H), 2.71 (t, 2H), 3.87 (t, 1H), 6.86 (d, 1H), 7.09 (s, 4H), 7.21 (s, 5H), 8.71 (d, 1H)

4-[4-(4-methoxyphenyl)-4-phenylbutyl]-1H-imidazole. M.p. of hydrochloride 156°–159° C.

$^1$H NMR (as HCl-salt, CDCl$_3$): 1.40–1.90 (m, 2H), 1.90–2.30 (m, 2H), 2.71 (t, 2H), 3.76 (s, 3H), 3.87 (t, 1H), 6.82 (d, 2H), 6.90 (s, 1H), 7.13 (d, 2H), 7.21 (m, 5H), 8.68 (s, 1H)

4-[4,4-bis(4-methoxyphenyl)butyl]-1H-imidazole. M.p. of hydrochloride 138°–142° C.

$^1$H NMR (as HCl-salt, CDCl$_3$): 1.40–2.25 (m, 4H), 2.71 (t, 2H), 3.75 (s, 6H) under which there is (t, 1H), 6.78 (d, 4H), 6.83 (s, 1H), 7.08 (d, 4H), 9.02 (s, 1H)

4-(4,5-diphenylpentyl)-1H-imidazole $^1$H NMR (as HCl-salt, CDCl$_3$): 1.20–1.90 (m, 4H), 2.57 (t, 2H), 2.83 (m, 3H), 6.71 (s, 1H), 6.80–7.40 (m, 10H), 8.84 (s, 1H)

4-(5,5-diphenylpentyl)-1H-imidazole $^1$H NMR (as HCl-salt, MeOH-d$_4$): 1.3–1.5 (m, 2H), 1.5–1.7 (m, 2H), 1.8–2.3 (m, 2H), 2.656 (t, 2H), 3.746 (t, 1H), 7.06–7.2 (m, 11H), 8.716 (d, 1H)

4-(6,6-diphenylhexyl)-1H-imidazole $^1$H NMR (as base, CDCl$_3$): 1.1–1.7 (m, 6H), 1.8–2.2 (m, 2H), 2.530 (t, 2H), 3.847 (t, 1H), 6.685 (s, 1H), 7.2 (s, 10H), 7.470 (s, 1H), 9.6 (broad s, 1H)

4-[4,4-bis(4-methylphenyl)butyl]-1H-imidazole. M.p. of hydrochloride 176°–179° C.

4-[4-(4-fluorophenyl)-4-phenylbutyl]-1H-imidazole. M.p. of hydrochloride 175°–182° C.

4-[4-(2-fluorophenyl)-4-phenylbutyl]-1H-imidazole. M.p. of hydrochloride 182°–190° C.

4-[4-(4-ethylphenyl)-4-phenylbutyl]-1H-imidazole $^1$H NMR (as HCl-salt, MeOH-d$_4$): 1.18 (t, 3H), 1.40–1.90 (m, 2H), 1.90–2.30 (m, 2H), 2.57 (q, 2H), 2.75 (t, 2H), 3.91 (t, 1H), 6.95–7.30 (m, 10H), 8.73 (d, 1H)

4-[4,4-bis(4-fluorophenyl)butyl]-1H-imidazole $^1$H NMR (as HCl-salt, MeOH-d$_4$): 1.40–1.85 (m, 2H), 1.90–2.30 (m, 2H), 2.77 (t, 2H), 3.98 (t, 1H), 6.80–7.40 (m, 9H), 8.72 (d, 1H)

EXAMPLE 2

4-[4-(4-fluorophenyl)-4-phenylbutyl]-1H-imidazole

A concentrated water solution of ammoniumformate (0,98 g, 15,6 mmol) is added dropwise to the boiling mixture of 1-benzyl-5-[4-(4-fluorophenyl)-4-phenylbutyl]-1H-imidazole (1,5 g, 3,9 mmol) and 10% Pd/C (0,156 g) in 16 ml of 50% ethanol. The mixture is refluxed for 2 hours. The catalyst is filtrated off and the solvent is evaporated. 2M NaOH is added and the product is extracted into ethyl acetate. The ethyl acetate phase is dried and evaporated to dryness to give the product. Yield 1,02 g. Melting point of the hydrochloride salt (from ethyl acetate) is 175°–182° C.

$^1$H NMR (as HCl-salt, MeOH-d$_4$): 1.40–1.90 (m, 2H), 1.90–2.30 (m, 2H), 2.75 (t, 2H), 3.96 (t, 1H), 6.85–7.36 (m, 10H), 8.74 (d, 1H)

According to the same procedure as the example the following substituted derivative was prepared:

4-[4-(2-fluorophenyl)-4-phenylbutyl]-1H-imidazole. M.p. of hydrochloride 182°–190° C.

$^1$H NMR (as HCl-salt, MeOH-d$_4$): 1.45–1.95 (m, 2H), 1.95–2.30 (m, 2H), 2.77 (t, 2H), 4.29 (t, 1H), 6.85–7.45 (m, 10H), 8.74 (d, 1H)

EXAMPLE 3

4-(4,4-diphenylbutyl)-1H-imidazole a) 1-benzyl-5-(4-hydroxy-4,4-diphenylbutyl)-1H-imidazole Magnesium turnings (0,49 g) are covered with 4 ml of dry tetrahydrofuran. Brombenzene (3,18 g) in 7 ml of dry tetrahydrofuran is added dropwise to the mixture at such a rate that a smooth reaction is maintained. The reaction mixture is refluxed for an additional hour. Ethyl 4-(1-benzyl-1H-imidazol-5-yl)butyrate (1,10 g) in 15 ml of dry tetrahydrofuran is then added dropwise to the Grignard reagent and the reaction mixture is refluxed for 2 hours. Saturated ammonium chloride is added to the cooled reaction mixture. Tetrahydrofuran is evaporated and the precipitated product is collected. Yield 1,41 g. Melting point of the hydrochloride salt is 197°–201° C.

$^1$H NMR (as HCl-salt, MeOH-d$_4$): 1.35–1.80 (m, 2H), 2.20–2.45 (m, 2H), 2.61 (t, 2H), 5.33 (s, 2H), 7.0–7.5 (m, 16H), 8.81 (d, 1H)

b) 1-benzyl-5-(4,4-diphenyl-3-butenyl)-1H-imidazole 1-benzyl-5-(4-hydroxy-4,4-diphenylbutyl)-1H-imidazole (1,3 g) is refluxed in 20 ml of ethanol containing 5% (w/w) hydrogen chloride for 1 hour. The solvent is evaporated and the HCl-salt of the product is precipitated with ethyl acetate. Yield 1,1 g, m.p. 161°–168° C.

$^1$H NMR (as HCl-salt, MeOH-d$_4$): 2.22–2.60 (m, 2H), 2.60–2.90 (m, 2H), 5.29 (s, 2H), 6.06 (t, 1H), 6.90–7.60 (m, 16H), 8.88 (d, 1H)

c) 1-benzyl-5-(4,4-diphenylbutyl)-1H-imidazole 1-benzyl-5-(4,4-diphenyl-3-butenyl)-1H-imidazole hydrochloride salt is hydrogenated in ethanol as described in Example 1 c). M.p. of the product as hydrochloride is 200°–202° C.

d) 4-(4,4-diphenylbutyl)-1H-imidazole

The benzyl group of 1-benzyl-5-(4,4-diphenylbutyl)-1H-imidazole is hydrogenated as is described in Example 1 d).

EXAMPLE 4

4-[4,4-bis(4-nitrophenyl)butyl]-1H-imidazole 1,8 g (14,6 mmol) of urea nitrate is added in small portions to a mixture of 2,0 g (7,3 mmol) of 4-(4,4-diphenylbutyl)-1H-imidazole in 6,4 ml of concentrated sulphuric acid under 10° C. The reaction mixture is stirred for 2 hours at room temperature. The mixture is made alkaline with 2M sodium hydroxide and the product is extracted into ethyl acetate. The product is purified by flash chromatography using methylene chloride-methanol (95:5) as eluent.

$^1$H NMR (as HCl-salt, MeOH-d$_4$): 1.4–1.95 (m, 2H), 2.0–2.45 (m, 2H), 2.81 (t, 2H), 4.34 (t, 1H), 7.27 (broad s, 1H), 7.5 (d, 4H), 8.17 (d, 4H), 8.73 (d, 1H)

EXAMPLE 5

4-[4,4-bis(4-aminophenyl)butyl]-1H-imidazole

4-[4,4-bis(4-nitrophenyl)butyl]-1H-imidazole is hydrogenated in ethanol using 10% palladium on carbon (Pd/C) as a catalyst.

$^1$H NMR (as HCl-salt, MeOH-d$_4$): 1.4–2.25 (m, 4H), 2.69 (t, 2H), 3.70 (t, 1H), 6.77 (d, 4H), 6.95 (d, 4H), 7.08 (broad s, 1H), 8.57 (d, 1H)

EXAMPLE 6

4-(4,4-diphenyl-1-butenyl)-1H-imidazole a) 4-(1-hydroxy-4,4-diphenylbutyl)-1H-imidazole A concentrated water solution of ammonium formate (4,0 g) is added dropwise to the boiling mixture of 1-benzyl-5-(1-hydroxy-4,4-diphenylbutyl)-1H-imidazole (4,5 g) and 10% Pd/C (0,5 g) in 50 ml of 50% ethanol. The mixture is refluxed for 2 hours. The catalyst is filtrated and the solvent is evaporated. 2M NaOH is added and the product is extracted into ethyl acetate. The ethyl acetate phase is dried and evaporated to dryness to give the product which is used in the following step b).

b) 4-(4,4-diphenyl-1-butenyl)-1H-imidazole 4-(1-hydroxy-4,4-diphenylbutyl)-1H-imidazole (3,0 g) and 20 g of anhydrous potassium hydrogen sulfate are heated at 150° C. for 4 hours. The mixture is cooled and 90 ml ethanol is added to dissolve the product. The mixture is made alkaline with sodium hydroxide. The product is extracted into methylene chloride, washed with water and evaporated to dryness. The product is then made to hydrochloride salt with dry hydrogen chloride in ethyl acetate. M.p. above 240° C.

$^1$H NMR (as HCl-salt, CDCl$_3$): 2.904–3.068 (m, 2H), 4.116 (t, 1H), 6.05–6.35 (m, 2H), 6.998 (d, 1H), 7.22–7.25 (m, 10H), 8.719 (d, 1H)

EXAMPLE 7

4-[1-(4-fluorophenyl)-5-phenylpentyl]-1H-imidazole a) 1-benzyl-5-(1-hydroxy-5-phenylpentyl)-1H-imidazole 2,1 g of magnesium turnings are covered with 60 ml of dry tetrahydrofuran. A solution of 4-phenylbutylbromide (18,8 g) in 20 ml of dry tetrahydrofuran is then added dropwise to the mixture at such a rate that a smooth reaction is maintained. After the addition is complete, the reaction mixture is refluxed for one additional hour and cooled to room temperature. The reaction mixture is then added dropwise to a solution of 1-benzyl-5-imidazolecarbaldehyde (6,5 g) in 80 ml of tetrahydrofuran at 60° C. After the addition is complete, the reaction mixture is refluxed for 2 hours, cooled and poured into cold water. Tetrahydrofuran is evaporated and conc. hydrochloric acid is added to the solution. The product which is separated as an oil, is extracted with methylene chloride and evaporated to dryness.

b) 4-(1-hydroxy-5-phenylpentyl)-1H-imidazole 1-benzyl-5-(1-hydroxy-5-phenylpentyl)-1H-imidazole hydrochloride (8,5 g), prepared in the Step a, is hydrogenated in the mixture of 100 ml of 2N hydrochloric acid and 10 ml of ethanol at 60° C. Pd/C (10%) as catalyst. When the uptake of the hydrogen ceases, the reaction mixture is cooled, filtered and evaporated to dryness. Water is added and the mixture is made alkaline with sodium hydroxide. The product is then extracted to methylene chloride which is washed with water, dried with sodium sulphate and evaporated to dryness. The residue is the product as base, and it is used as such in Step c.

$^1$H NMR (as base, MeOH-d$_4$+a drop of CDCl$_3$): 1.2–2.0 (m, 6H), 2.61 (distorted t, 2H), 4.65 (t, 1H), 6.91 (dd, 1H), 7.0–7.3 (m, 5H), 7.56 (d, 1H)

c) 4-(1-oxo-5-phenylpentyl)-1H-imidazole 5,5 g of 4-(1-hydroxy-5-phenylpentyl)-1H-imidazole and 7,0 g of manganese dioxide are refluxed stirring in tetrachloroethylene for four hours. The reaction mixture is filtered and the filtrate is evaporated to dryness. Water is added and the product is extracted into methylene chloride. The combined extracts are washed with water and evaporated to dryness.

d) 4-[1-(4-fluorophenyl)-1-hydroxy-5-phenylpentyl]-1H-imidazole 0,52 g of magnesium turnings are covered with 60 ml of dry tetrahydrofuran. Then a solution of 1-bromo-4-fluorobenzene (3,8 g) in 60 ml of dry tetrahydrofuran is added dropwise to the mixture at such a rate that a smooth reaction is maintained. After the addition is complete, the reaction mixture is refluxed for one additional hour and cooled to room temperature. The reaction mixture is then added dropwise to a solution of 4-(1-oxo-5-phenylpentyl)-1H-imidazole (3,8 g) in 40 ml of tetrahydrofuran at 60° C. After the addition is complete, the reaction mixture is refluxed for 3 hours, cooled and poured into cold water. Tetrahydrofuran is evaporated and conc. hydrochloric acid is added to the solution. The product is extracted as hydrochloric salt into methylene chloride. Combined methylene chloride extracts are then evaporated to dryness.

e) 4-[1-(4-fluorophenyl)-5-phenyl-1-pentenyl]-1H-imidazole

4-[1-(4-fluorophenyl)-1-hydroxy-5-phenylpentyl]-1H-imidazole hydrochloride (5,0 g) and 30,0 g of anhydrous potassium hydrogen sulphate are heated at 150° C. for 4 hours. The mixture is cooled and 90 ml of ethanol is added to dissolve the product. The mixture is then filtered and the filtrate is evaporated to minor volume. Water is added and the mixture is made alkaline with sodium hydroxide. The product is extracted into methylene chloride, washed with water and evaporated to dryness. The product is then made to hydrochloride salt with dry hydrogen chloride in dry ethylacetate.

$^1$H NMR (as base, CDCl$_3$): 1.5–2.7 (m, 6H), 4.8 (broad s, 1H), 6.34 (t, 1H), 6.48 (broad s, 1H), 6.9–7.4 (m, 9H), 7.52 (broad s, 1H)

Using the same method for example the following compounds included in the invention were prepared:
4-[1-(4-fluorophenyl)-5-(3-methylphenyl)-1-pentenyl]-1H-imidazole
4-[1-(4-fluorophenyl)-5-(4-methylphenyl)-1-pentenyl]-1H-imidazole
4-[1-(4-fluorophenyl)-5-(2-methylphenyl)-1-pentenyl]-1H-imidazole
4-[5-(3,5-dimethylphenyl)-1-(4-fluorophenyl)-1-pentenyl]-1H-imidazole
4-[1-(4-fluorophenyl)-5-(3-methoxyphenyl)-1-pentenyl]-1H-imidazole
4-[5-(3,5-dimethoxyphenyl)-1-(4-fluorophenyl)-1-pentenyl]-1H-imidazole f) 4-[1-(4-fluorophenyl)-5-phenylpentyl]-1H-imidazole 4-[1-(4-fluorophenyl)-5-phenyl-1-pentenyl]-1H-imidazole hydrochloride (2,0 g) is dissolved in ethanol and a catalytic amount 10% Pd/C is added. The reaction mixture is agitated vigorously at room temperature in a hydrogen atmosphere until the uptake of hydrogen ceases. The mixture is filtered and the filtrate is evaporated to dryness. The residue which is the product is purified by flash chromatography eluting with methylene chloride-methanol mixture. Yield 82%.

$^1$H NMR (as base, CDCl$_3$): 1.1–2.7 (m, 8H), 3.84 (t, 1H), 6.71 (broad s, 1H), 6.80–7.38 (m, 9H), 7.47 (broad s, 1H), 9.22 (broad s, 1H)

Using the same method for example the following compounds included in the invention were prepared:
4-[1-(4-fluorophenyl)-5-(3-methylphenyl)pentyl]-1H-imidazole MS: 322 (20, M+·), 189 (28), 176 (38), 175 (72), 149 (100), 125 (20), 121 (14), 109 (42), 105 (16), 97 (21)

$^1$H NMR (as HCl-salt, MeOH-d$_4$): 1.1–2.7 (m, 8H), 2.27 (s, 3H), 4.06 (t, 1H), 6.7–7.5 (m, 8H), 7.37 (d, 1H), 8.77 (d, 1H)
4-[1-(4-fluorophenyl)-5-(4-methylphenyl)pentyl]-1H-imidazole $^1$H NMR (as HCl-salt, MeOH-d$_4$): 1.1–2.7 (m, 8H), 2.26 (s, 3H), 4.05 (t, 1H), 6.8–7.6 (m, 9H), 8.78 (d, 1H)
4-[1-(4-fluorophenyl)-5-(2-methylphenyl)pentyl]-1H-imidazole MS: 322 (53, M+·), 189 (30), 176 (55), 175 (100), 148 (18), 121 (12), 105 (42), 101 (11), 79 (12), 77 (13)

$^1$H NMR (as HCl-salt, MeOH-d$_4$): 1.1–2.7 (m, 8H), 2.24 (s, 3H), 4.11 (t, 1H), 6.9–7.5 (m, 9H), 8.79 (d, 1H)
4-[5-(3,5-dimethylphenyl)-1-(4-fluorophenyl)pentyl]-1H-imidazole MS: 336 (47, M+·), 189 (90), 176 (67), 175 (100), 166 (13), 148 (16), 121 (12), 119 (16), 91 (14)

$^1$H NMR (as HCl-salt, MeOH-d$_4$): 1.1–2.6 (m, 8H), 2.22 (s, 6H), 4.09 (t, 1H), 6.6–7.4 (m, 7H), 7.40 (broad s, 1H), 8.80 (broad s, 1H)
4-[1-(4-fluorophenyl)-5-(3-methoxyphenyl)pentyl]-1H-imidazole
4-[5-(3,5-dimethoxyphenyl)-1-(4-fluorophenyl)pentyl]-1H-imidazole

EXAMPLE 8

4-(1,3-diphenylpropyl)-1H-imidazole a) 1-benzyl-5-(1-oxo-3-phenylpropyl)-1H-imidazole 1-benzyl-5-(1-hydroxy-3-phenylpropyl)-1H-imidazole is oxidized with manganese dioxide in tetrachloroethylene, as it is described in Example 7 c).

$^1$H NMR (as base, CDCl$_3$): 3.03 (m, 4H), 5.53 (s, 2H), 7.07–7.4 (m, 10H), 7.60 (s, 1H), 7.77 (s, 1H)

Using the same method for example the following compounds included in the invention were prepared:
1-benzyl-5-[5-(2,6-dimethylphenyl)-1-oxopentyl]-1H-imidazole. M.p. of hydrochloride 175°–180° C.
1-benzyl-5-(1-oxo-5-phenylpentyl)-1H-imidazole. M.p. of hydrochloride 185°–189° C.

b) 1-benzyl-5-(1-hydroxy-1,3-diphenylpropyl)-1H-imidazole

Grignard reagent is prepared from 5,0 g of bromobenzene and 0,76 g of Mg turnings in tetrahydrofuran. This solution is then added to 3,1 g of 1-benzyl-5-(1-oxo-3-phenylpropyl)-1H-imidazole in tetrahydrofuran and the reaction mixture is refluxed for 3 hours. The mixture is then poured into cold water, tetrahydrofuran is evaporated and the solution is made acidic with hydrochloric acid. The hydrochloride of the product is filtered, washed with toluene and dried. M.p. 196°–198° C.

Using the same method for example the following compounds included in the invention were prepared:
1-benzyl-5-(1-hydroxy-1,5-diphenylpentyl)-1H-imidazole. M.p. of hydrochloride 193°–196° C.
1-benzyl-5-[5-(2,6-dimethylphenyl)-1-hydroxy-1-phenylpentyl]-1H-imidazole. M.p. of hydrochloride 190°–192° C.

c) 1-benzyl-5-(1,3-diphenylpropyl)-1H-imidazole 1-benzyl-5-(1-hydroxy-1,3-diphenylpropyl)-1H-imidazole is treated with anhydrous potassium hydrogen sulphate at 150° C. as described in Example 7 e). The double bond of the obtained intermediate, 1-benzyl-5-(1,3-diphenyl-1-propenyl)-1H-imidazole, is hydrogenated as described in Example 7 f). M.p. of the hydrochloride salt is 154°–174° C. (from diethylether).

$^1$H NMR (as HCl-salt, MeOH-d$_4$): 2.2–2.7 (m, 4H), 3.90 (t, 1H), 5.12 (AB q, the middle of the quartet, 2H), 6.90–7.37 (m, 15H), 7.70 (broad s, 1H), 8.88 (d, 1H)

Using the same method for example the following compounds were prepared:
1-benzyl-5-(1,5-diphenylpentyl)-1H-imidazole $^1$H NMR (as base, CDCl$_3$): 1.18–2.61 (m, 8H), 3.56 (t, 1H), 4.59 and 4.81 (AB q, 2H), 6.76–7.40 (m, 17H)
1-benzyl-5-[5-(2,6-dimethylphenyl)-1-phenylpentyl]-1H-imidazole d) 4-(1,3-diphenylpropyl)-1H-imidazole 1-benzyl-5-(1,3-diphenylpropyl)-1H-imidazole is hydrogenated in the mixture of 2N hydrochloric acid and ethanol at 60° C. 10% Pd/C as catalyst. The product is isolated as in Example 7 b) and is purified by flash chromatography methylene chloride-methanol (9,5:0,5) as eluent. Yield 73%.

$^1$H NMR (as base, CDCl$_3$): 2.1–2.7 (m, 4H), 3.88 (t, 1H), 6.71 (broad s, 1H), 7.01–7.26 (m, 10H), 7.30 (d, 1H), 10.5 (broad s, 1H)

Using the same method for example the following compound was prepared:

4-(1,5-diphenylpentyl)-1H-imidazole

¹H NMR (as HCl-salt, MeOH-d₄): 1.2–2.3 (m, 6H), 2.57 (distorted t, 2H), 4.05 (t, 1H), 7.05–7.40 (m, 11H), 8.73 (d, 1H)

EXAMPLE 9

1-benzyl-4-(1,3-diphenylpropyl)-1H-imidazole 2,0 g of benzylbromide in 5 ml of toluene is added dropwise to the mixture of 4-(1,3-diphenylpropyl)-1H-imidazole (2,6 g), 48% NaOH (10 ml), toluene (20 ml) and tetrabutylammoniumbromide (0,2 g) at room temperature. After addition the reaction mixture is stirred at room temperature for 3 hours. Water is added and the toluene layer is separated. The toluene phase is then washed with water and evaporated to dryness. The residue contains the isomers 1-benzyl-4-(1,3-diphenylpropyl)-1H-imidazole and 1-benzyl-5-(1,3-diphenylpropyl)-1H-imidazole and the former is separated and purified by flash chromatography (methylene chloride-methanol 9,5:0,5).

EXAMPLE 10

4-[1,4-bis(4-fluorophenyl)butyl]-1H-imidazole a) 1-benzyl-5-[1-(4-fluorophenyl)-1-hydroxymethyl]-1H-imidazole Grignard reaction of 4-bromofluorobenzene and 1-benzyl-5-imidazolecarbaldehyde is performed analogously to Example 7 a). The product is crystallized as hydrochloride salt from ethylacetate. Yield 94%.

¹H NMR (as base, CDCl₃+MeOH-d₄): 5.05 and 5.21 (AB q, 2H), 5.64 (s, 1H), 6.61 (s, 1H), 6.97–7.1 (m, 4H), 7.26–7.33 (m, 5H), 7.41 (s, 1H)

MS: 282 (22, M⁺·), 265 (5), 191 (18), 91 (100)

b) 1-benzyl-5-[1-(4-fluorophenyl)-1-oxomethyl]-1H-imidazole

Oxidation of 1-benzyl-5-[1-(4-fluorophenyl)-1-hydroxymethyl]-1H-imidazole is performed analogously to Example 7 c). The crude product is recrystallized as a base from methanol. Yield 72%.

¹H NMR (as base, CDCl₃): 5.62 (s, 2H), 7.1–7.4 (m, 7H), 7.5–8.0 (m, 4H)

MS: 280 (46, M⁺·), 123 (13), 107 (4), 95 (19), 91 (100)

c) 1-benzyl-5-[1,4-bis(4-fluorophenyl)-1-hydroxybutyl]-1H-imidazole 1-benzyl-5-[1,4-bis(4-fluorophenyl)-1-hydroxybutyl]-1H-imidazole is prepared analogously to Example 7 a) starting from 3-(4-fluorophenyl)-1-bromopropane and 1-benzyl-5-[1-(4-fluorophenyl)-1-oxomethyl]-1H-imidazole. The product is purified by flash chromatography.

¹H NMR (as base, CDCl₃): 1.2–1.4 (m, 1H), 1.65–1.85 (m, 1H), 2.1–2.25 (m, 2H), 2.52 (t, 2H), 4.73 and 4.81 (AB q, 2H), 6.75–7.3 (m, 15H)

Using the same method for example the following compounds included in the invention were prepared:

1-benzyl-5-[1-(4-fluorophenyl)-1-hydroxy-3-phenylpropyl]-1H-imidazole

MS: 386 (M⁺·, 8), 368 (22), 281 (100), 159 (26), 91 (99), 65 (34)

1-benzyl-5-[1,3-bis(4-fluorophenyl)-1-hydroxypropyl]-1H-imidazole

MS: 404 (M⁺·, 2), 386 (18), 195 (16), 281 (33), 123 (34), 91 (100), 65 (20)

1-benzyl-5-[1-(4-fluorophenyl)-1-hydroxy-4-phenylbutyl]-1H-imidazole

MS: 400 (M⁺·, 2), 382 (2), 281 (38), 191 (3), 91 (100), 65 (9)

1-benzyl-5-[1-(4-fluorophenyl)-1-hydroxy-5-(3-methoxyphenyl)pentyl]-1H-imidazole ¹H NMR (as HCl-salt, MeOH-d₄): 1.0–1.8 (m, 4H), 2.26 (t, 2H), 2.52 (t, 2H), 4.71 (s, 3H), 5.06 and 5.31 (ABq, 2H), 6.6–7.5 (m, 13H), 7.7 (s, 1H), 8.6 (s, 1H)

1-benzyl-5-[5-(2,6-dimethylphenyl)-1-(4-fluorophenyl)-1-hydroxypentyl]-1H-imidazole

MS: 442 (M⁺·, 19), 281 (71), 256 (5), 191 (7), 119 (21), 91 (100)

d) 4-[1,4-bis(4-fluorophenyl)butyl]-1H-imidazole 1-benzyl-5-[1,4-bis(4-fluorophenyl)-1-hydroxybutyl]-1H-imidazole (10 g) is dissolved in conc. acetic acid (100 ml). Into the solution is added 0,1 g of palladium on carbon and 0,8 g of ammoniumformate. The mixture is refluxed for an hour and cooled to room temperature. The solution is filtered through silicous earth. The acetic acid filtrate is evaporated, the residue is dissolved in methylene chloride and washed once with 2M aqueous sodium hydroxide solution and once with water. The methylene chloride solution is dried with sodium sulphate and evaporated under reduced pressure. The product is then made to hydrochloride salt with dry hydrogen chloride in diethylether. M.p. 135°–137° C.

¹H NMR (as base, CDCl₃): 1.4–1.65 (m, 2H), 1.8–1.95 (m, 1H), 2.05–2.2 (m, 1H), 2.5–2.65 (m, 2H), 3.87 (t, 1H), 6.7 (s, 1H), 6.8–7.2 (m, 8H), 7.5 (s, 1H)

Using the same method for example the following compounds included in the invention were prepared:

4-[1-(4-fluorophenyl)-3-phenylpropyl]-1H-imidazole

¹H NMR (as base, CDCl₃): 2.0–2.7 (m, 4H), 3.7–4.0 (m, 1H), 6.7 (s, 1H), 6.75–7.45 (m, 9H), 7.57 (s, 1H)

MS: 280 (4, M⁺·), 189 (9), 176 (100), 148 (15), 121 (9), 91 (12)

4-[1,3-bis(4-fluorophenyl)propyl]-1H-imidazole

¹H NMR (as base, CDCl₃): 2.1–2.25 (m, 1H), 2.3–2.6 (m, 3H), 3.88 (t, 1H), 6.76 (s, 1H), 6.9–7.2 (m, 8H), 7.63 (s, 1H)

MS: 298 (5, M⁺·), 189 (8), 176 (100), 122 (22), 109 (42)

4-[1-(4-fluorophenyl)-4-phenylbutyl]-1H-imidazole

¹H NMR (as base, CDCl₃): 1.3–2.3 (m, 4H), 2.6 (t, 2H), 3.88 (t, 1H), 6.67 (s, 1H), 6.7–7.3 (m, 9H), 7.39 (s, 1H)

MS: 294 (31, M⁺·), 189 (24), 175 (100), 91 (31)

4-[1-(4-fluorophenyl)-5-(3-methoxyphenyl)pentyl]-1H-imidazole

¹H NMR (as base, CDCl₃): 1.1–2.3 (m, 6H), 2.5 (t, 2H), 3.76 (s, 3H), 3.85 (distorted t, 1H), 6.6–7.6 (m, 10H)

MS: 338 (19, M⁺·), 189 (43), 175 (70), 148 (12), 121 (20), 36 (100)

4-[1-(4-fluorophenyl)-5-(4-methoxyphenyl)pentyl]-1H-imidazole

¹H NMR (as base, CDCl₃): 1.1–2.3 (m, 6H), 2.49 (t, 2H), 3.75 (s, 3H), 3.8 (distorted t, 1H), 6.6–7.6 (m, 10H)

MS: 338 (10, M⁺·), 189 (20), 175 (22), 148 (6), 121 (22), 36 (100)

4-[5-(2,6-dimethylphenyl)-1-(4-fluorophenyl)pentyl]-1H-imidazole

¹H NMR (as base, CDCl₃): 1.25–1.5 (m, 4H), 1.8–1.95 (m, 1H), 2.05–2.2 (m, 1H), 2.25 (s, 6H), 2.52 (t, 2H), 3.86 (t, 1H), 6.71 (s, 1H), 6.9–7.0 (m, 5H), 7.1–7.2 (m, 2H), 7.4 (s, 1H)

MS: 336 (50, M⁺·), 217 (20), 189 (75), 175 (100), 148 (13), 119 (23)

EXAMPLE 11

1-benzyl-5-[1-(4-fluorophenyl)-3-phenyl-1-propenyl]-1H-imidazole

Titanium tetrachloride (0,03 mol) is added dropwise to a stirred suspension of zinc powder (0,06 mol) in tetrahydrofuran (30 ml) at −10° C. under dry nitrogen. The mixture is heated to reflux and refluxing is continued for 1 hour. The solution is cooled to 0° C. and 1-benzyl-5-[1-(4-fluorophenyl)-1-oxomethyl]-1H-imidazole (0,005 mol) in tetrahydrofuran (10 ml) and phenylacetaldehyde (0,006 mol) in tetrahydrofuran (10 ml) are added into the mixture, respectively. The mixture is refluxed with stirring for 1 hour. The dark mixture is poured into water (60 ml), tetrahydrofuran is evaporated and the mixture is extracted with methylene chloride (2×100 ml). The methylene chloride solution is washed with 2N sodium hydroxide and water, dried with sodium sulphate and evaporated to dryness. The residue is purified by flash chromatography.

$^1$H NMR (as base, CDCl$_3$): 3.35 and 3.45 (2d, 2H), 4.62 and 4.65 (2s, 2H), 6.03 and 6.20 (2t, 1H), 6,8–7.3 (m, 15H), 7.50 and 7.64 (2s, 1H).

EXAMPLE 12

4-[1,3-bis(4-nitrophenyl)propyl]-1H-imidazole 1,8 g (14,6 mmol) of urea nitrate is added in small portions to a mixture of 2,7 g (7,3 mmol) of 4-(1,3-diphenylpropyl)-1H-imidazole in 6,4 ml of concentrated sulphuric acid under 10° C. The reaction mixture is stirred for 2 hours at room temperature. The mixture is made alkaline with 2M sodium hydroxide and the product is purified by flash chromatography using methylene chloride-methanol (95:5) as eluent.

EXAMPLE 13 a) 1-benzyl-5-[2-(4-fluorophenyl)-4-phenyl-1-butenyl]-1H-imidazole

A flask is charged with Zn (41,7 g, 0,642 mol) and 200 ml of tetrahydrofuran. TiCl$_4$ (60,3 g, 0,321 mol) is added dropwise to the mixture at 0° C. to 10° C. and then the mixture is refluxed for an hour. 12,2 g (0,054 mol) 4′-fluoropropiophenone and 14,9 g (0,080 mol) 1-benzyl-5-imidazolylaldehyde in 250 ml of THF is added to the mixture at room temperature. The mixture is heated to boiling and the refluxing is continued for three hours. After cooling to room temperature the mixture is poured to 10% K$_2$CO$_3$-solution. Toluene is added and the mixture is filtered through siliceous earth. The toluene phase is separated and the water layer is extracted again with toluene. The toluene extracts are combined, washed with water, dried with MgSO$_4$ and evaporated to dryness. The crude product is purified by flash chromatography with methylene chloride and methanol (9,75:0,25) as eluent.

MS: 382 (14,M+·), 291 (34), 200 (4), 91 (100)

Using the same method for example the following compounds included in the invention were prepared:
1-benzyl-5-(2,4-diphenyl-1-butenyl)-1H-imidazole MS: 364 (30,M+·), 273 (72), 182 (9), 91 (100), 65 (11)
1-benzyl-5-[2,4-bis(4-fluorophenyl)-1-butenyl]-1H-imidazole

MS: 400 (31,M+·), 291 (73), 200 (9), 109 (35), 91 (100)

$^1$H NMR (as HCl-salt, CDCl$_3$): 2.62 (broken t, 2H), 2.82 (broken t, 2H), 5.34 (s, 2H), 6.20 (s, 1H), 6.43 (s, 1H), 6.86–7.5 (m, 13H), 8.93 (s, 1H).

b) 4-[2-(4-fluorophenyl)-4-phenylbutyl]-1H-imidazole
1-benzyl-5-[2-(4-fluorophenyl)-4-phenyl-1-butenyl]-1H-imidazole (4,58 g, 0,0012 mol) is dissolved in ethanol-water-solution (25:15). 0,46 g of 10% Pd/C and 3,8 g (0,06 mol) of ammoniumformate in 15 ml of water is added to the mixture. After refluxing for 2 hours the mixture is filtered and the filtrate is evaporated to dryness. The residue is dissolved into methylene chloride and washed a few times with water. Methylene chloride is evaporated and the residue is dissolved into 2M hydrogen chloride solution. The solution is extracted twice with diethyl ether. The water layer is made alkaline and extracted with methylene chloride. The methylene chloride phase is dried and evaporated to dryness. The product is then made to hydrochloride salt with dry hydrogen chloride gas in diethyl ether.

MS: 294 (12,M+·), 203 (36), 190 (28), 109 (28), 91 (100), 82 (42)

Using the same method for example the following compounds included in the invention were prepared:
4-(2,4-diphenylbutyl)-1H-imidazole

MS: 276 (14,M+·), 185 (31), 172 (24), 91 (100), 82 (43)

$^1$H NMR (as base, CDCl$_3$): 1.9–2.1 (m, 2H), 2.4–2.5 (m, 2H), 2.8–3.0 (m, 3H), 6.53 (s, 1H), 7.0–7.4 (m, 11H)
4-[2,4-bis(4-fluorophenyl)butyl]-1H-imidazole

MS: 312 (4,M+·), 203 (16), 190 (22), 109 (100), 91 (9), 81 (52)

$^1$H NMR (as HCl-salt, MeOH-d$_4$): 1.95–2.1 (m, 2H), 2.4–2.5 (m, 2H), 2.9–3.1 (m, 3H), 6.9–7.25 (m, 9H), 8.68 (s, 1H).

EXAMPLE 14

4-[2-(4-cyanophenyl)-4-(4-fluorophenyl)butyl]-1H-imidazole a) 1-benzyl-5-[2-(4-cyanophenyl)-4-(4-fluorophenyl)-1-butenyl]-1H-imidazole 4,46 g of titanium tetrachloride is added dropwise to a stirred suspension of zinc powder (3,08 g) in tetrahydrofuran (50 ml) at −10° C. under dry nitrogen. The mixture is heated to reflux and refluxing is continued for one hour. The solution is cooled to room temperature and 1,0 g of 4-(4-cyanophenyl)-3-(4-fluorophenyl)-propan-1-one in 25 ml of tetrahydrofuran and 0,73 g of 1-benzyl-5-imidazolecarbaldehyde in 25 ml of tetrahydrofuran are added into the mixture, respectively. The mixture is stirred at room temperature for 2 hours and refluxed for 6 hours. The dark mixture is poured into water (60 ml), rendered alkaline with 10% potassium carbonate solution and extracted with toluene. The toluene solution is filtered through siliceous earth, the filtrate is evaporated and the residue is purified by flash chromatography.

MS: 407 (M+·, 8), 298 (35), 109 (13), 91 (100)

b) 4-[2-(4-cyanophenyl)-4-(4-fluorophenyl)butyl-1H-imidazole 1-benzyl-5-[2-(4-cyanophenyl)-4-(4-fluorophenyl)-1-butenyl]-1H-imidazole hydrochloride is dissolved in ethanol and a catalytic amount of 10% Pd/C is added. The reaction mixture is agitated vigorously at room temperature in a hydrogen atmosphere until the reduction and the debenzylation are complete. The reaction mixture is filtered and evaporated to dryness. The product is purified by flash chromatography.

$^1$H NMR (as HCl-salt, MeOH-d$_4$): 2.0–2.15 (m, 2H), 2.46 (t, 2H), 3.0–3.16 (m, 3H), 6.96 (t, 2H), 7.0–7.11 (m, 3H), 7.38 (d, 2H), 7.68 (d, 2H), 8.70 (s, 1H).

We claim:

1. A compound which is a 4(5) substituted imidazole of the formula:

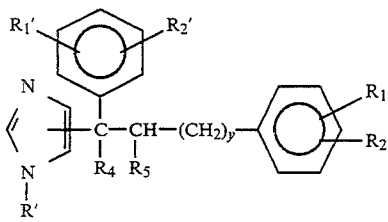

(Ib)

or a non-toxic pharmaceutically acceptable acid addition salt thereof wherein $R_1$, $R_2$, $R'_1$ and $R'_2$, which can be the same or different, are H, $CH_3$, $C_2H_5$, $C_3H_7$, $OCH_3$, OH, $CH_2OH$, $NO_2$, $NH_2$, CN, $CF_3$, $CHF_2$, $CH_2F$ or halogen; R' is H or

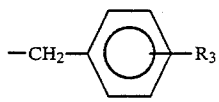

where $R_3$ is H, $CH_3$ or halogen; $R_4$ is H or OH and $R_5$ is H or $R_4$ and $R_5$ together form a bond and y is 1 to 4.

2. A substituted imidazole according to claim 1 wherein $R_4$, $R_5$ and R' each are H.

3. A substituted imidazole according to claim 2 wherein $R_1$, $R_2$ and $R'_2$ each are H and $R'_1$ which is as defined in claim 1, is in the para position of the phenyl group.

4. A substituted imidazole according to claim 3 wherein $R'_1$ is F.

5. A substituted imidazole according to claim 2 wherein $R_2$ and $R'_2$ each are H and $R_1$, which is as defined in claim 1, is in the ortho, meta or para position of the phenyl group and $R'_1$, which is as defined in claim 1, is in the para position of the phenyl group.

6. A substituted imidazole according to claim 5 wherein $R_2$ and $R'_2$ both are H and $R_1$ and $R'_1$, which are as defined in claim 1, both are in the para position of the phenyl group.

7. A substituted imidazole according to claim 6 wherein $R_1$ and $R'_1$ both are F.

8. A substituted imidazole according to claim 6 wherein $R_1$ is $CH_3$ and $R'_1$ is F.

9. A substituted imidazole according to claim 2 wherein $R'_2$ is H, $R'_1$, which is as defined in claim 1, is in the para position of the phenyl group and $R_1$ and $R_2$, which are defined as in claim 1, are in the 3 and 5 positions of the phenyl group.

10. A substituted imidazole according to claim 2 wherein $R'_2$ is H, $R'_1$, which is as defined in claim 1, is in the para position of the phenyl group and $R_1$ and $R_2$, which are as defined in claim 1, are in the 2 and 6 positions of the phenyl group.

11. A compound according to claim 1 which is 4-[1-(4-fluorophenyl)-5-phenylpentyl]-1H-imidazole or a non-toxic pharmaceutically acceptable acid addition salt thereof.

12. A compound according to claim 1 which is 4-[1-(4-fluorophenyl)-5-(2-methylphenyl)pentyl]-1H-imidazole or a non-toxic pharmaceutically acceptable acid addition salt thereof.

13. A compound according to claim 1 which is 4-[1-(4-fluorophenyl)-5-(3-methylphenyl)pentyl]-1H-imidazole or a non-toxic pharmaceutically acceptable acid addition salt thereof.

14. A compound according to claim 1 which is 4-[1-(4-fluorophenyl)-5-(3-methylphenyl)pentyl]-1H-imidazole or a non-toxic pharmaceutically acceptable acid addition salt thereof.

15. A compound according to claim 1 which is 4-[5-(3,5-dimethylphenyl)-1-(4-fluorophenyl)pentyl]-1H-imidazole or a non-toxic pharmaceutically acceptable acid addition salt thereof.

16. A compound according to claim 1 which is 4-(1,5-diphenylpentyl)-1H-imidazole or a non-toxic pharmaceutically acceptable acid addition salt thereof.

17. A compound according to claim 1 which is 4-(1,3-diphenylpropyl)-1H-imidazole or a non-toxic pharmaceutically acceptable acid addition salt thereof.

18. A compound according to claim 1 which is 1-benzyl-5-(1,3-diphenylpropyl)-1H-imidazole or a non-toxic pharmaceutically acceptable acid addition salt thereof.

19. A compound according to claim 1 which is 4-(1-(4-fluorophenyl)-3-phenylpropyl]-1H-imidazole or a non-toxic pharmaceutically acceptable acid addition salt thereof.

20. A compound according to claim 1 which is 4-[1-(4-fluorophenyl)-4-phenylbutyl]-1H-imidazole or a non-toxic pharmaceutically acceptable acid addition salt thereof.

21. A compound according to claim 1 which is 4-[1-(4-fluorophenyl)-5-(3-methoxyphenyl)pentyl]-1H-imidazole or a non-toxic pharmaceutically acceptable acid addition salt thereof.

22. A compound according to claim 1 which is 4-[1-(4-fluorophenyl)-5-(4-methoxyphenyl)pentyl]-1H-imidazole or a non-toxic pharmaceutically acceptable acid addition salt thereof.

23. A compound according to claim 1 which is 4-[1-(4-fluorophenyl)-5-(2,6-dimethylphenyl)pentyl]-1H-imidazole or a non-toxic pharmaceutically acceptable acid addition salt thereof.

24. A compound according to claim 1 which is 4-[1,3-bis(4-fluorophenyl)propyl]-1H-imidazole or a non-toxic pharmaceutically acceptable acid addition salt thereof.

25. A compound according to claim 1 which is 4-[1,4-bis(4-fluorophenyl)butyl]-1H-imidazole or a non-toxic pharmaceutically acceptable acid addition salt thereof.

26. A pharmaceutical composition suitable for use in inhibiting aromatase comprising an amount of a compound as claimed in claim 1 effective to inhibit aromatase, and a pharmaceutically acceptable carrier.

27. A method of inhibiting aromatase comprising administering to a subject in which such inhibition is desired, an amount of a compound as claimed in claim 1 effective to produce the desired inhibition.

* * * * *

UNITED STATES PATENT AND TRADEMARK OFFICE
CERTIFICATE OF CORRECTION

PATENT NO. : 5,439,928
DATED : August 8, 1995
INVENTOR(S) : Arto Johannes KARJALAINEN et al.

It is certified that error appears in the above-indentified patent and that said Letters Patent is hereby corrected as shown below:

On the title page, column 1, after "761,550, Sep. 18, 1991, abandoned.", please insert:

item [30]      Foreign Application Priority Data

Mar. 30, 1989 [GB]   United Kingdom . . . . . . . . . . . . . . 8907218.5

Mar. 31, 1989 [GB]   United Kingdom . . . . . . . . . . . . . . 8907309.2

Sep. 21, 1990 [GB]   United Kingdom . . . . . . . . . . . . . . 9020629.3--

Signed and Sealed this

Twenty-second Day of October, 1996

Attest:

BRUCE LEHMAN

*Attesting Officer*      *Commissioner of Patents and Trademarks*